(12) United States Patent
Aoki et al.

(10) Patent No.: US 7,776,918 B2
(45) Date of Patent: Aug. 17, 2010

(54) REMEDY FOR VIRAL DISEASE

(75) Inventors: Masahiro Aoki, Kamakura (JP);
Hideyuki Kato, Kamakura (JP);
Masayuki Sudoh, Kamakura (JP);
Takuo Tsukuda, Kamakura (JP);
Miyako Masubuchi, Kamakura (JP);
Kenichi Kawasaki, Kamakura (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 1405 days.

(21) Appl. No.: 10/544,896

(22) PCT Filed: Feb. 12, 2004

(86) PCT No.: PCT/JP2004/001498

§ 371 (c)(1),
(2), (4) Date: Aug. 8, 2005

(87) PCT Pub. No.: WO2004/071503

PCT Pub. Date: Aug. 26, 2004

(65) Prior Publication Data

US 2006/0217434 A1    Sep. 28, 2006

(30) Foreign Application Priority Data

Feb. 12, 2003  (JP) ............................. 2003-034056
Jul. 9, 2003   (JP) ............................. 2003-272420

(51) Int. Cl.
*A01N 37/12*    (2006.01)
*A01N 43/38*    (2006.01)

(52) U.S. Cl. ..................... 514/563; 514/419; 514/534

(58) Field of Classification Search .................. 514/563
See application file for complete search history.

(56) References Cited

FOREIGN PATENT DOCUMENTS

| EP | 0 526 936 A2 | 2/1993 |
| EP | 1 002 793 A1 | 5/2000 |
| WO | WO 93/24660 A1 | 12/2003 |
| WO | WO 94/18157 A1 | 8/2004 |

OTHER PUBLICATIONS

Fleisch, H. (Biphosphonates: Mechanisms of action, Endocrine reviews 19(1): 80-100), Printed pp. 1-49, especially p. 5, 7th paragraph.*
Palaska et al. (Synthesis and antidepressant activities of some 3,5-diphenyl-2-pyrazolines, European Journal of Medicinal Chemistry, vol. 36, Issue 6, Jun. 2001, pp. 539-543).*
The Epidemiology Program Office (EPO, hereinafter), Centers for Disease Control and Prevention (CDC) U.S. Department of Health and Human Services, Atlanta, GA. 30333, United States Department of Health and Human Services (Recommendations for Prevention and Control of Hepatitis C Virus (HCV) Infection and HCV-related Chronic Disease, Oct. 16, 1998.*
Esumi et al., Synthesis of viridiofungin a trimethyl ester and determination of the absolute structure of viridiofungin A, Tetrahedron Letters/ vol. 39, Issue 8, 1998, pp. 877-880, printed pp. 1-3.*
V. Lohmann et al., "Replication of Subgenomic Hepatitis C Virus RNAs in a Hepatoma Cell Line," Reports, Science, vol. 285, pp. 110-113, Jul. 2, 1999.
Supplementary European Search Report dated Apr. 3, 2009 in corresponding European patent application 04710509.3, 2 pages.
Hanada et al., "Serine palmitoyltransferase, a key enzyme of sphingolipid metabolish," Biochimica et Biophysica Acta, Jun. 10, 2003, 1632(1-3):16-30.
Mandala et al., "Viridiofungins, Novel Inhibitors of Sphingolipid Synthesis," The Journal of Antibiotics, Apr. 1, 1997, 50(4):339-343.
Bordier et al., "A Prenylation Inhibitor Prevent Production of Infectious Hapatitis Delta Virus Particle," Journal of Virology, vol. 76, No. 20, 2002, pp. 10465-10472.
Esumi et al., "Synthesis of Viridiofungin A Trimethyl Ester and Determination of the Absolute Structure of Viridiofungin A," Tetrahedron Letters, vol. 39, No. 8, 1998, pp. 877-880.

* cited by examiner

*Primary Examiner*—Sreeni Padmanabhan
*Assistant Examiner*—Timothy E Betton
(74) *Attorney, Agent, or Firm*—Foley & Lardner LLP

(57) ABSTRACT

The object of the present invention is to provide a pharmaceutical composition for preventing or treating viral infectious diseases. The compounds of the present invention have extremely potent anti-HCV activity and HCV growth inhibitory effects, and since they also only demonstrate mild cytotoxicity in vivo, a pharmaceutical composition containing the compound of the present invention is extremely useful as an anti-HCV preventive/therapeutic agent.

8 Claims, No Drawings

REMEDY FOR VIRAL DISEASE

TECHNICAL FIELD

The present invention relates to a pharmaceutical composition for preventing and treating liver diseases caused by viral infectious diseases, and particularly infection by HCV.

BACKGROUND ART

There are 100 to 200 million persons infected with hepatitis C virus (HCV) throughout the world, and there are estimated to be more than 2 million infected persons in Japan. Approximately 50% of these patients progress to chronic hepatitis, approximately 20% of those patients progress to cirrhosis and liver cancer thirty years or more after infection. Roughly 90% of the cases of liver cancer are said to be caused by hepatitis C. In Japan, more than 20,000 patients each year die from liver cancer concomitant to HCV infection.

HCV was discovered in 1989 as the primary causative virus of non-A, non-B hepatitis following transfusion. HCV is an RNA virus having an envelope, and its genome is composed of a single-stranded (+) RNA. It is classified as a hepacivirus belonging to the Flavivirus family.

Since HCV avoids the host's immune mechanism for reasons that are as yet unclear, there are many cases in which a sustained infection results even when the virus has infected adults having a developed immune mechanism. It then progresses to chronic hepatitis, cirrhosis and liver cancer, and there are known to be a large number of patients in which liver cancer recurs due to inflammation occurring at non-cancerous sites even if excised surgically.

Accordingly, there is a desire to establish an effective method of treatment for hepatitis C, and aside from nosotropic methods which suppress inflammation through the use of anti-inflammatory drugs, there is a particularly strong public desire for the development of a drug that is capable of reducing or eradicating HCV in the affected site of the liver.

At present, interferon treatment is the only known treatment method that is effective in eliminating HCV. However, interferon is effective only in about one-third of all patients. The efficacy of interferon against HCV genotype 1b in particular is extremely low. Thus, it is strongly desired to develop an anti-HCV drug that can be used in place of or in combination with interferon.

In recent years, although ribavirin (1-β-D-ribofuranosyl-1H-1,2,4-triazole-3-carboxyamide) has been sold commercially as a therapeutic drug for hepatitis C by concomitant use with interferon, its efficacy remains low, and new hepatitis C therapeutic drugs are sought after. In addition, although attempts have been made to eliminate the virus by enhancing patient immunity through the use of interferon agonists, interleukin-12 agonists and so forth, none of these have been found to be effective.

Ever since cloning of the HCV gene, although molecular biological analyses have progressed rapidly on the mechanisms and functions of virus genes and the functions of various viral proteins, mechanisms involving virus replication within host cells, sustained infection, pathogenicity and so forth have yet to be fully elucidated. At present, a reliable testing system for HCV infection using cultured cells has not been established. Thus, it has so far been required to use substitute virus assay methods using other allied viruses when evaluating anti-HCV drugs.

In recent years however, it has become possible to observe HCV replication in vitro using a non-structural domain portion of HCV. As a result, anti-HCV drugs can now be evaluated easily by the replicon assay method (Non-Patent Document 1). The mechanism of HCV RNA replication in this system is considered to be the same as the replication of the entire length of the HCV RNA genome that has infected hepatocytes. Thus, this system can be said to be an assay system that is based on cells useful for identifying compounds that inhibit HCV replication.

The compounds claimed in the present patent are compounds which inhibit HCV replication that were found using the aforementioned replicon assay method. These inhibitors are considered to have a high possibility of serving as HCV therapeutic drugs.

Non-Patent Document 1:

V. Lohmann, et al., ed., Science, 1999, Vol. 285, p. 110-113.

The object of the present invention is to provide a pharmaceutical composition for preventing and treating liver diseases caused by viral infectious diseases, and particularly HCV infection.

As a result of earnestly conducting research to solve the aforementioned problems, the inventors of the present invention found that the compounds of the present invention have extremely potent anti-HCV replicon activity and effects that inhibit proliferation of HCV, demonstrate only mild cytotoxicity in vitro, and are extremely useful as anti-HCV preventive/therapeutic agents, thereby leading to completion of the present invention.

DISCLOSURE OF THE INVENTION

Namely, the present invention provides the following (1) to (3).

(1) A pharmaceutical composition for preventing or treating viral infectious diseases such as HCV comprising a compound represented by the following general formula (I):

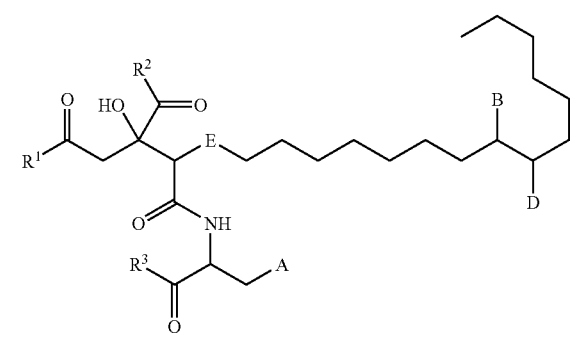

(wherein

A represents a phenyl group substituted with —OX, or a 3-indolyl group;

X represents a hydrogen atom, a linear or branched alkyl group having 1 to 8 carbon atoms, a linear or branched alkenyl group having 2 to 8 carbon atoms, or a linear or branched alkynyl group having 2 to 8 carbon atoms;

B represents a hydrogen atom, a hydroxyl group, an oxo group, —N($R^4$) ($R^5$), =N—OH, =N—$OR^6$ or a halogen atom;

$R^4$ and $R^5$ may be the same or different, and each represent a hydrogen atom, a linear or branched alkyl group having 1 to 6 carbon atoms, a linear or branched alkenyl group having 2 to 6 carbon atoms, or a linear or branched alkynyl group having 2 to 6 carbon atoms, or $R^4$ and $R^5$ together represent a 3 to 8 membered ring (for example, piperazine ring, pyrrolidine ring, piperidine ring, morpholine ring or hexamethylene imine ring);

$R^6$ represents a linear or branched alkyl group having 1 to 8 carbon atoms (which may be substituted with an amino group which may be mono- or di-substituted with a linear or branched alkyl group having 1 to 4 carbon atoms);

D represents a hydrogen atom or a hydroxyl group;

E represents a single bond or double bond;

$R^1$, $R^2$ and $R^3$ may be the same or different, and each represent a hydrogen atom, a hydroxyl group, an amino group (which may be mono- or di-substituted with a linear or branched alkyl group having 1 to 4 carbon atoms), —OZ, a linear or branched alkyl group having 1 to 4 carbon atoms, a linear or branched alkenyl group having 2 to 4 carbon atoms, or a linear or branched alkynyl group having 2 to 4 carbon atoms; and, Z represents a linear or branched alkyl group having 1 to 4 carbon atoms, a linear or branched alkenyl group having 2 to 4 carbon atoms, or a linear or branched alkynyl group having 2 to 4 carbon atoms), a prodrug thereof, or a pharmaceutically acceptable salt thereof.

(2) A compound represented by the aforementioned general formula (I) (wherein each of the symbols in the formula have the same meanings as in the aforementioned general formula (I), with the proviso that the case in which A is a 3-indolyl group, the case in which A is a phenyl group substituted with —OX at the p position, X is a 2-isopentenyl group or a hydrogen atom, B is an oxo group, D is a hydrogen atom, E represents a double bond, and all of $R^1$ to $R^3$ are a hydroxyl group, and the case in which A is a phenyl group substituted with —OX at position p, X is a 2-isopentenyl group, B is an oxo group, D is a hydrogen atom, bond E represents a double bond, and all of $R^1$ to $R^3$ are a methoxy group are excluded), a prodrug thereof, or a pharmaceutically acceptable salt thereof.

(3) A compound represented by the aforementioned general formula (I) (wherein each of the symbols in the formula have the same meanings as in the aforementioned general formula (I), with the proviso that the case in which A is a 3-indolyl group, the case in which A is a phenyl group substituted with —OX at position p and X is a hydrogen atom, and the case in which A is a phenyl group substituted with —OX at position p, X is a 2-isopentenyl group, B is an oxo group, D is a hydrogen atom, bond E represents a double bond, and all of $R^1$ to $R^3$ are a hydroxyl group or a methoxy group are excluded), a prodrug thereof, or a pharmaceutically acceptable salt thereof.

BEST MODE FOR CARRYING OUT THE INVENTION

The following provides a more detailed explanation of the pharmaceutical composition for preventing and/or treating diseases caused by virus infections such as HCV of the present invention.

It should be noted that, the term "treatment" used in the present specification includes the eradication or reduction of HCV by administering the pharmaceutical composition of the present invention to a subject to be tested, the suppression of further HCV proliferation, and the alleviation of symptoms caused by HCV infection. Examples of symptoms caused by HCV infection include hepatitis C, cirrhosis, liver fibrosis and liver cancer, and preferably hepatitis C.

In addition, the linear or branched alkenyl groups having 2 to 8 carbon atoms used in the present specification refer to linear or branched hydrocarbon groups having carbon atoms that contain at least one double bond. In addition, the linear or branched alkynyl groups having 2 to 8 carbon atoms refer to linear or branched hydrocarbon groups having 2 to 8 carbon atoms that contain at least one triple bond.

The "prodrug" of the present invention refers to a derivative of the compound of formula (I) that is converted to the compound of formula (I) or a pharmaceutically acceptable salt thereof under physiological conditions or by solvolysis. Although the prodrug may be inert when administered to a patient, it is present in the body after being converted to the active compound of formula (I).

The present invention is as indicated below.

1. A pharmaceutical composition for preventing or treating viral infectious diseases comprising a compound represented by the following general formula (I):

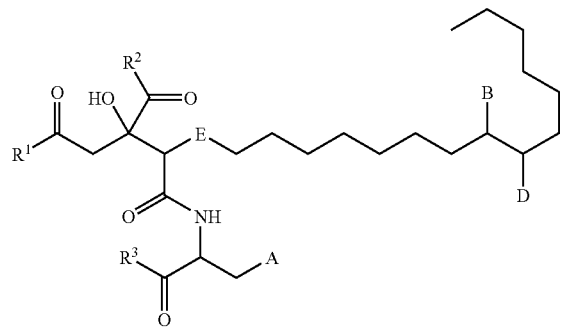

(wherein

A represents a phenyl group substituted with —OX, or a 3-indolyl group;

X represents a hydrogen atom, a linear or branched alkyl group having 1 to 8 carbon atoms, a linear or branched alkenyl group having 2 to 8 carbon atoms, or a linear or branched alkynyl group having 2 to 8 carbon atoms;

B represents a hydrogen atom, a hydroxyl group, an oxo group, —N($R^4$)($R^5$), =N—OH, =N—$OR^6$ or a halogen atom;

$R^4$ and $R^5$ may be the same or different, and each represent a hydrogen atom, a linear or branched alkyl group having 1 to 6 carbon atoms, a linear or branched alkenyl group having 2 to 6 carbon atoms, or a linear or branched alkynyl group having 2 to 6 carbon atoms, or $R^4$ and $R^5$ together represent a 3 to 8 membered ring;

$R^6$ represents a linear or branched alkyl group having 1 to 8 carbon atoms (which may be substituted with an amino group which may be mono- or di-substituted with a linear or branched alkyl group having 1 to 4 carbon atoms);

D represents a hydrogen atom or a hydroxyl group;

bond E represents a single bond or double bond;

$R^1$, $R^2$ and $R^3$ may be the same or different, and each represent a hydrogen atom, a hydroxyl group, an amino group (which may be mono- or di-substituted with a linear or branched alkyl group having 1 to 4 carbon atoms), —OZ, a linear or branched alkyl group having 1 to 4 carbon atoms, a linear or branched alkenyl group having 2 to 4 carbon atoms, or a linear or branched alkynyl group having 2 to 4 carbon atoms; and, Z represents a linear or branched alkyl group having 1 to 4 carbon atoms, a linear or branched alkenyl group having 2 to 4 carbon atoms, or a linear or branched alkynyl group having 2 to 4 carbon atoms) a prodrug thereof or a pharmaceutically acceptable salt thereof.

2. The pharmaceutical composition according to the above-mentioned 1 comprising the compound of formula (I) according to the above-mentioned 1 represented by the following general formula (I'), a prodrug thereof or a pharmaceutically acceptable salt thereof:

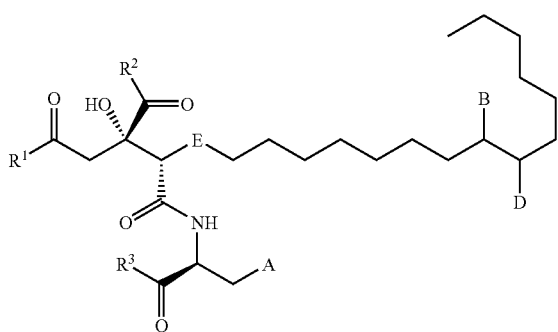

(wherein A, B, D, bond E, $R^1$, $R^2$ and $R^3$ are the same as described in the aforementioned 1).

3. The pharmaceutical composition according to the above-mentioned 1 or 2 comprising a compound of formula (I), a prodrug thereof or a pharmaceutically acceptable salt thereof wherein, A represents a phenyl group substituted with —OX at position 4, X represents a hydrogen atom, a linear or branched alkyl group having 1 to 8 carbon atoms, a linear or branched alkenyl group having 2 to 8 carbon atoms, or a linear or branched alkynyl group having 2 to 8 carbon atoms.

4. The pharmaceutical composition according to any one of the above-mentioned 1 to 3 comprising a compound of formula (I), a prodrug thereof or a pharmaceutically acceptable salt thereof, wherein B represents an oxo group, a hydrogen atom, a hydroxyl group or =N—$OR^6$.

5. The pharmaceutical composition according to any one of the above-mentioned 1 to 4 comprising a compound of formula (I), a prodrug thereof or a pharmaceutically acceptable salt thereof, wherein $R^1$, $R^2$ and $R^3$ may be the same or different and each represent a hydroxyl group, an amino group, or —OZ (wherein Z represents a linear or branched alkyl group having 1 to 4 carbon atoms).

6. The pharmaceutical composition according to the above-mentioned 1 or 2 comprising a compound of formula (I), a prodrug thereof or a pharmaceutically acceptable salt thereof, wherein A represents a phenyl group substituted with —OX at position 4, X represents a hydrogen atom, a linear or branched alkyl group having 1 to 8 carbon atoms, a linear or branched alkenyl group having 2 to 8 carbon atoms or a linear or branched alkynyl group having 2 to 8 carbon atoms, B represents an oxo group, a hydroxyl group or =N—$OR^6$, and $R^1$, $R^2$ and $R^3$ may be the same or different and each represent a hydroxyl group or —OZ (wherein Z represents a linear or branched alkyl group having 1 to 4 carbon atoms).

7. The pharmaceutical composition according to the above-mentioned 6 comprising a compound of formula (I), a prodrug thereof or a pharmaceutically acceptable salt thereof, wherein X represents a linear or branched alkyl group having 1 to 8 carbon atoms, a linear or branched alkenyl group having 2 to 8 carbon atoms or a linear or branched alkynyl group having 2 to 8 carbon atoms, B represents an oxo group or a hydroxyl group, and $R^1$, $R^2$ and $R^3$ each represent a hydroxyl group.

8. The pharmaceutical composition according to the above-mentioned 1 or 2 comprising a compound of formula (I), a prodrug thereof or a pharmaceutically acceptable salt thereof, wherein A represents a 3-indolyl group.

9. The pharmaceutical composition according to the above-mentioned 8 comprising a compound of formula (I), a prodrug thereof or a pharmaceutically acceptable salt thereof, wherein B represents an oxo group or a hydroxyl group, and $R^1$, $R^2$ and $R^3$ each represent a hydroxyl group.

10. The pharmaceutical composition according to the above-mentioned 1 or 2 comprising a compound of formula (I), a prodrug thereof of a pharmaceutically acceptable salt thereof, selected from the compounds indicated below.

No. 1

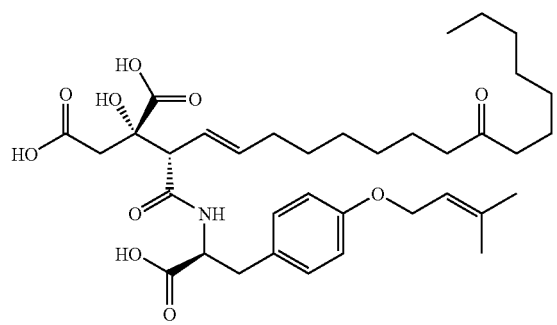

No. 2

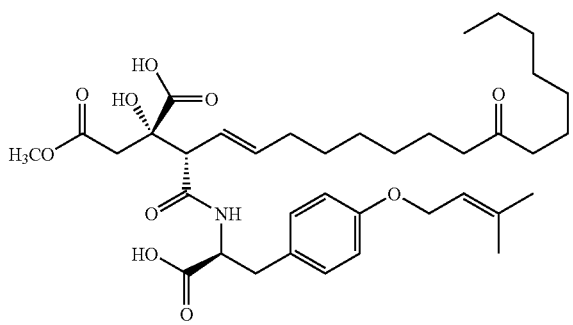

-continued
No. 3
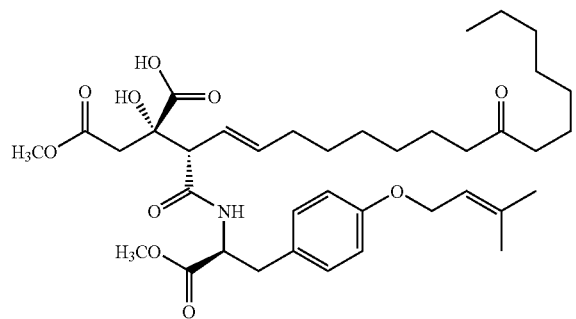
No. 4
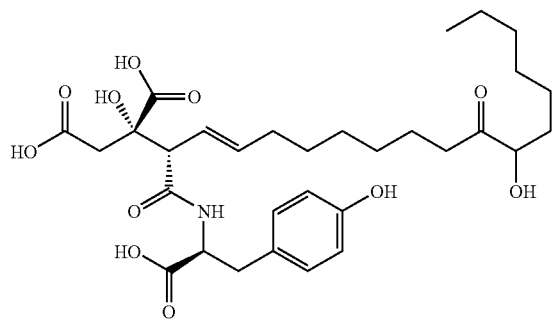
No. 5
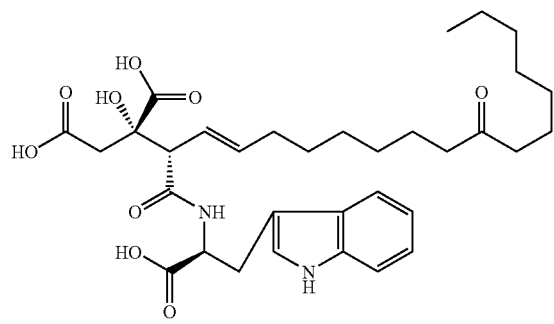
No. 6
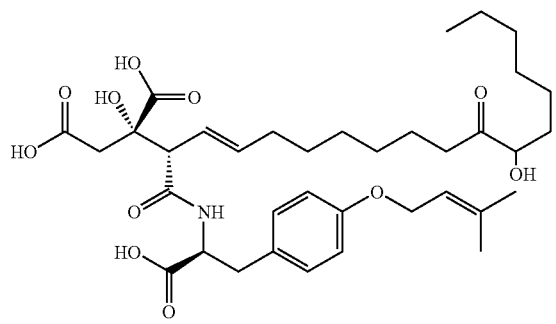
No. 7
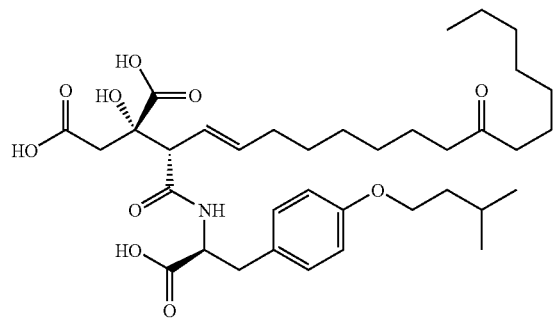
No. 8
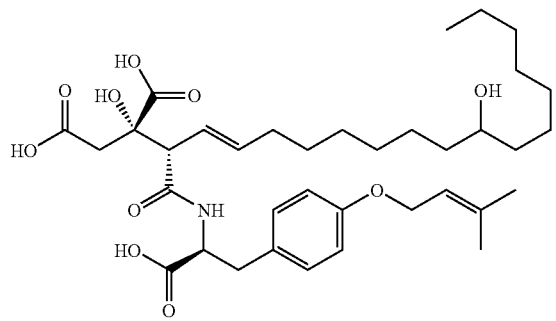
No. 9
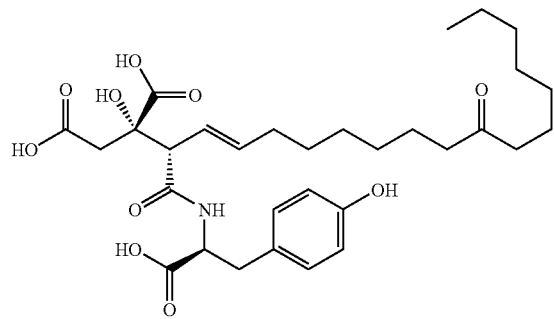
No. 10
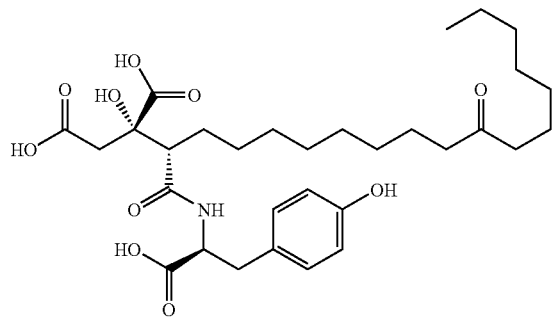

-continued
No. 11
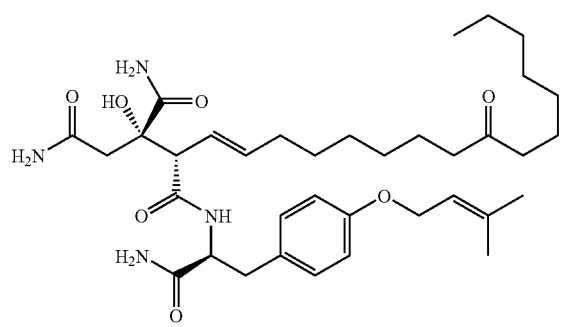
No. 12
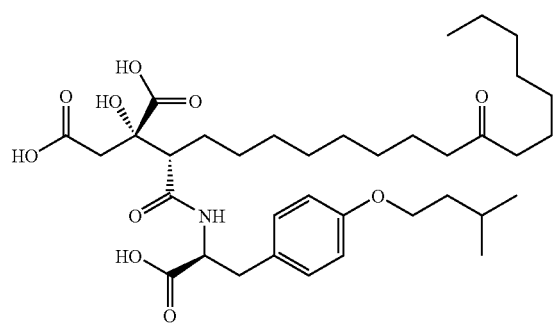
No. 13
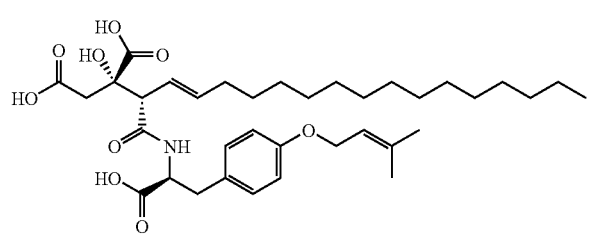
No. 14
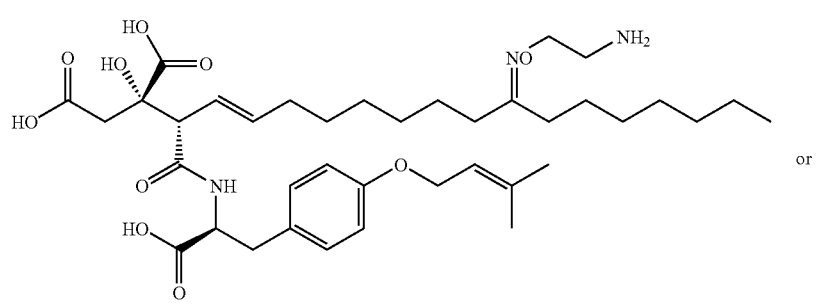
or
No. 15
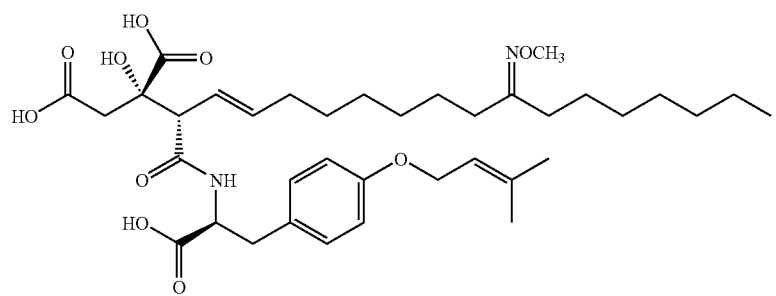

11. The pharmaceutical composition according to the abovementioned 1 or 2 comprising a compound of formula (I), a prodrug thereof or a pharmaceutically acceptable salt thereof, selected from the compounds indicated below.
No. 1
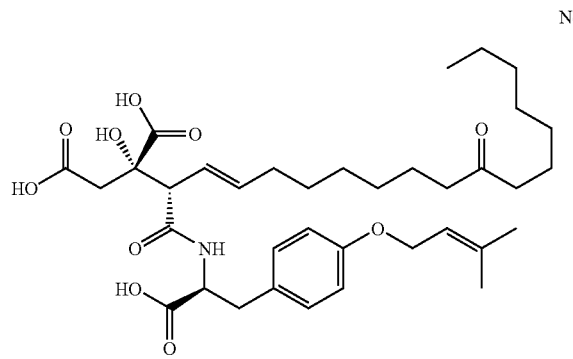
No. 3
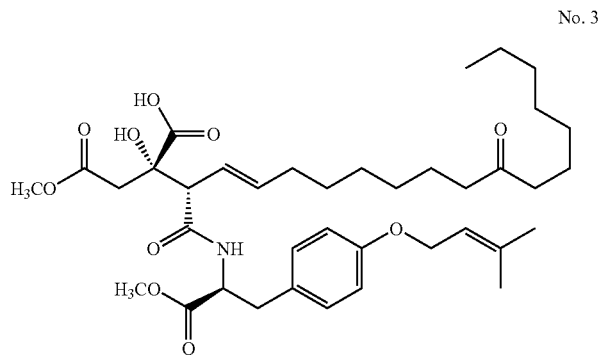
No. 5
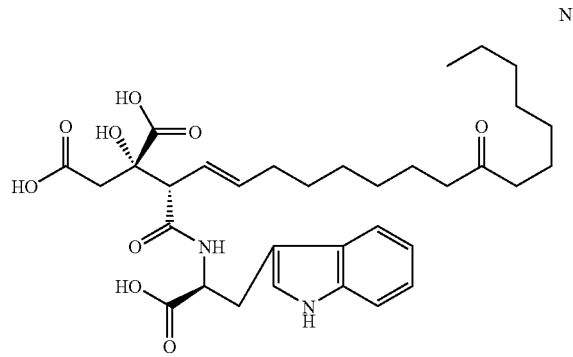
No. 6
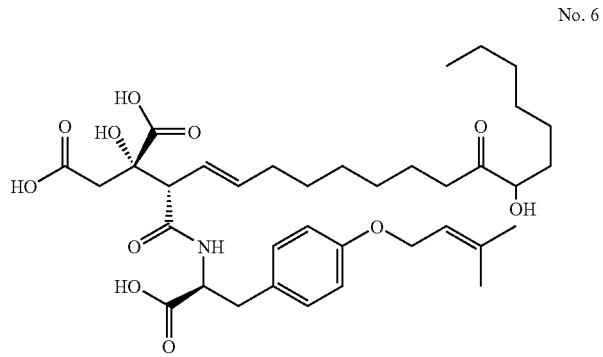
No. 7
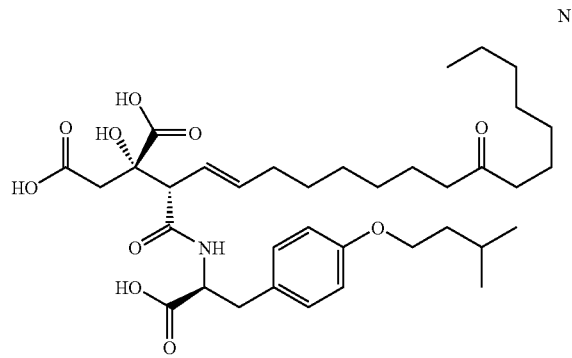
No. 8
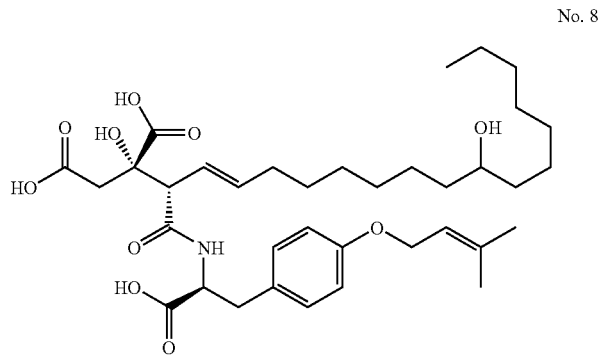
No. 9
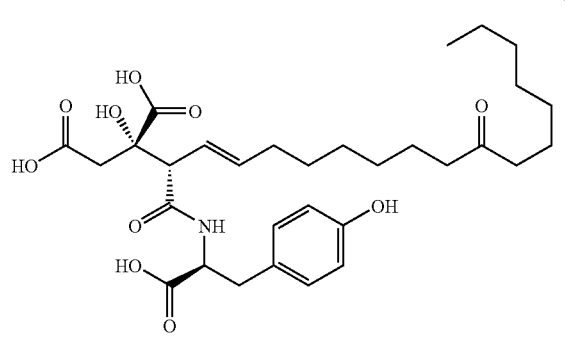
No. 12
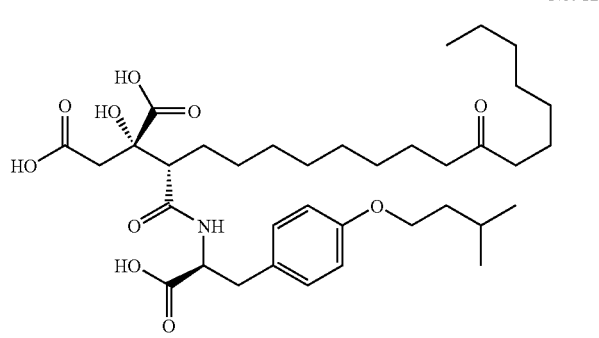

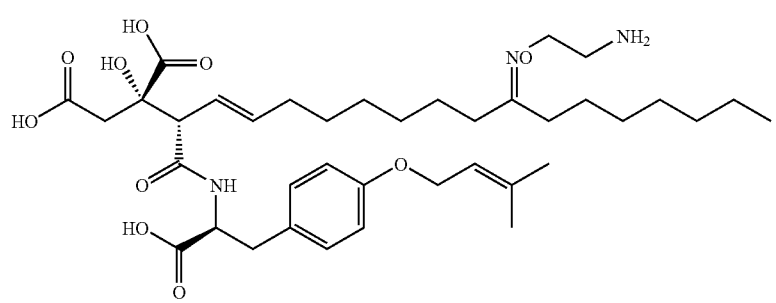

No. 14 or

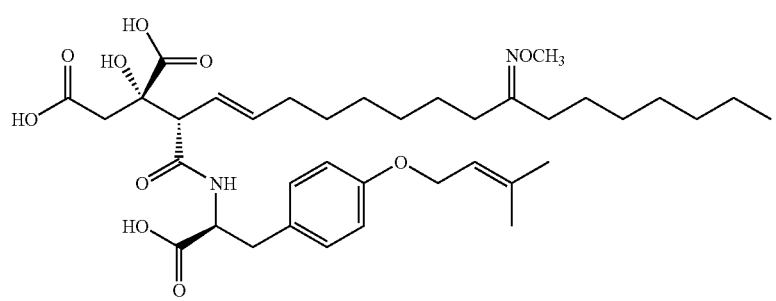

No. 15

12. The pharmaceutical composition according to the above-mentioned 1 or 2 comprising a compound of formula (I), a prodrug thereof or a pharmaceutically acceptable salt thereof, selected from the compounds indicated below.

No. 1

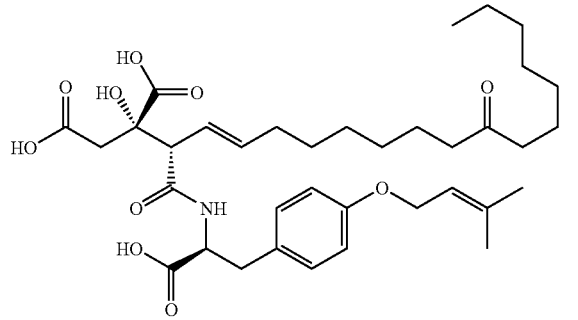

No. 6

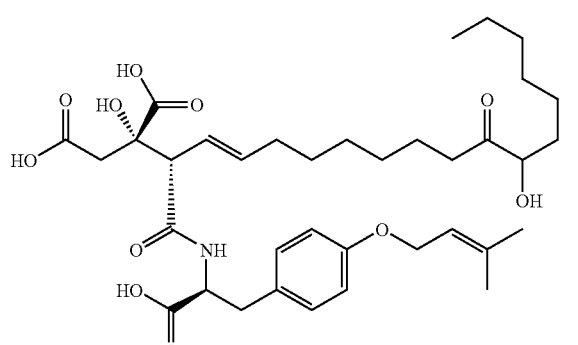

-continued

No. 7

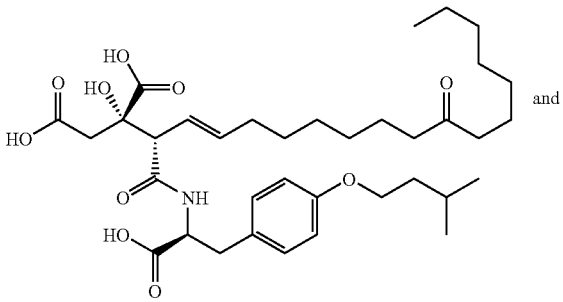

and

No. 8

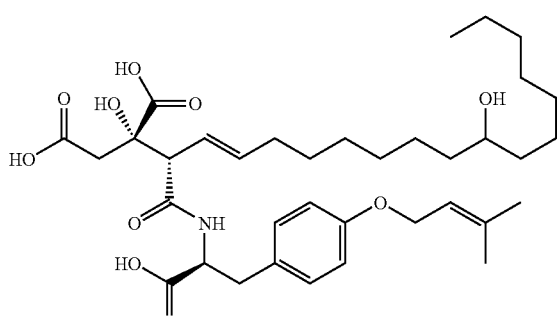

13. The pharmaceutical composition according to any one of the above-mentioned 1 to 12, wherein the viral infectious disease HCV infection.

14. The pharmaceutical composition according to the above-mentioned 13, wherein the HCV infection is hepatitis C.

15. A compound represented by the following general formula (I):

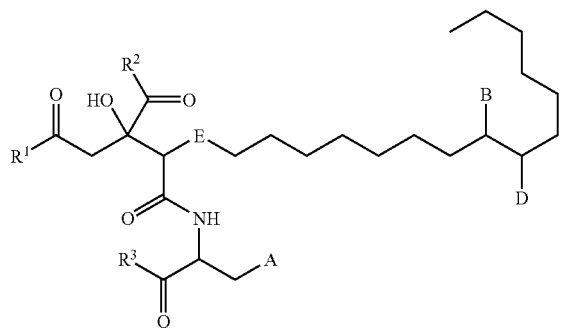
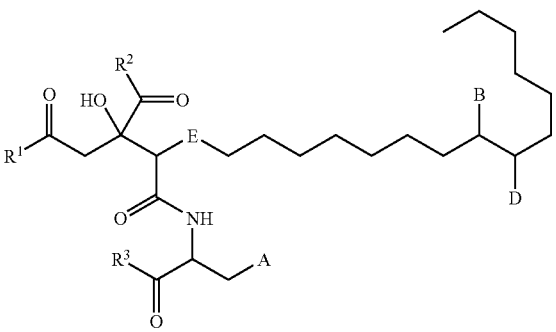

(wherein

A represents a phenyl group substituted with —OX;

X represents a hydrogen atom, a linear or branched alkyl group having 1 to 8 carbon atoms, a linear or branched alkenyl group having 2 to 8 carbon atoms, or a linear or branched alkynyl group having 2 to 8 carbon atoms;

B represents a hydrogen atom, a hydroxyl group, an oxo group, —N($R^4$)($R^5$), =N—OH, =N—$OR^6$ or a halogen atom;

$R^4$ and $R^5$ may be the same or different, and each represent a hydrogen atom, a linear or branched alkyl group having 1 to 6 carbon atoms, a linear or branched alkenyl group having 2 to 6 carbon atoms, or a linear or branched alkynyl group having 2 to 6 carbon atoms, or $R^4$ and $R^5$ together represent a 3 to 8 member ring;

$R^6$ represents a linear or branched alkyl group having 1 to 8 carbon atoms (which may be substituted with an amino group which may be mono- or di-substituted with a linear or branched alkyl group having 1 to 4 carbon atoms);

D represents a hydrogen atom or a hydroxyl group;

bond E represents a single bond or double bond;

$R^1$, $R^2$ and $R^3$ may be the same or different, and each represent a hydrogen atom, a hydroxyl group, an amino group (which may be mono- or di-substituted with a linear or branched alkyl group having 1 to 4 carbon atoms), —OZ, a linear or branched alkyl group having 1 to 4 carbon atoms, a linear or branched alkenyl group having 2 to 4 carbon atoms, or a linear or branched alkynyl group having 2 to 4 carbon atoms; and, Z represents a linear or branched alkyl group having 1 to 4 carbon atoms, a linear or branched alkenyl group having 2 to 4 carbon atoms, or a linear or branched alkynyl group having 2 to 4 carbon atoms, with the proviso that the case in which A is a phenyl group substituted with —OX at the p position, X is a 2-isopentenyl group or a hydrogen atom, B is an oxo group, D is a hydrogen atom, E represents a double bond, and all of $R^1$ to $R^3$ are a hydroxyl group, and the case in which A is a phenyl group substituted with —OX at position p, X is a 2-isopentenyl group, B is an oxo group, D is a hydrogen atom, bond E represents a double bond, and all of $R^1$ to $R^3$ are a methoxy group are excluded)

a prodrug thereof or a pharmaceutically acceptable salt thereof.

16. A compound represented by the following general formula (I):

(wherein

A represents a phenyl group substituted with —OX;

X represents a hydrogen atom, a linear or branched alkyl group having 1 to 8 carbon atoms, a linear or branched alkenyl group having 2 to 8 carbon atoms, or a linear or branched alkynyl group having 2 to 8 carbon atoms;

B represents a hydrogen atom, a hydroxyl group, an oxo group, —N($R^4$)($R^5$), =N—OH, =N—$OR^6$ or a halogen atom;

$R^4$ and $R^5$ may be the same or different, and each represent a hydrogen atom, a linear or branched alkyl group having 1 to 6 carbon atoms, a linear or branched alkenyl group having 2 to 6 carbon atoms, or a linear or branched alkynyl group having 2 to 6 carbon atoms, or $R^4$ and $R^5$ together represent a 3 to 8 membered ring;

$R^6$ represents a linear or branched alkyl group having 1 to 8 carbon atoms (which may be substituted with an amino group which may be mono- or di-substituted with a linear or branched alkyl group having 1 to 4 carbon atoms);

D represents a hydrogen atom or a hydroxyl group;

bond E represents a single bond or double bond;

$R^1$, $R^2$ and $R^3$ may be the same or different, and each represent a hydrogen atom, a hydroxyl group, an amino group (which may be mono- or di-substituted with a linear or branched alkyl group having 1 to 4 carbon atoms), —OZ, a linear or branched alkyl group having 1 to 4 carbon atoms, a linear or branched alkenyl group having 2 to 4 carbon atoms, or a linear or branched alkynyl group having 2 to 4 carbon atoms; and, Z represents a linear or branched alkyl group having 1 to 4 carbon atoms, a linear or branched alkenyl group having 2 to 4 carbon atoms, or a linear or branched alkynyl group having 2 to 4 carbon atoms, with the proviso that the case in which A is a phenyl group substituted with —OX at position p and X is a hydrogen atom, and the case in which A is a phenyl group substituted with —OX at position p, X is a 2-isopentenyl group, B is an oxo group, D is a hydrogen atom, bond E indicates a double bond, and all of $R^1$ to $R^3$ are a hydroxyl group or a methoxy group are excluded)

a prodrug thereof or a pharmaceutically acceptable salt thereof

17. The compound of formula (I) according to the above-mentioned 15 or 16 represented by the following general formula (I'), a prodrug thereof or a pharmaceutically acceptable salt thereof:

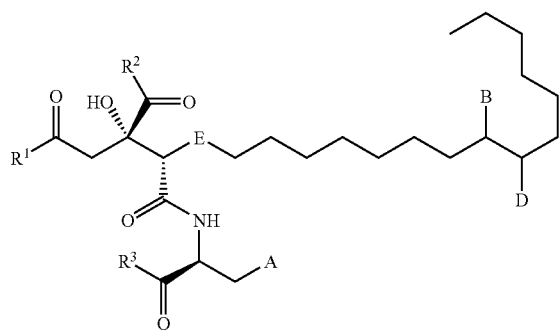

(wherein A, B, D, bond E, $R^1$, $R^2$ and $R^3$ are the same as described in the above-mentioned 15).

18. The compound of formula (I) according to the above-mentioned 15 to 17, a prodrug thereof or a pharmaceutically acceptable salt thereof, wherein X represents a linear or branched alkyl group having 1 to 8 carbon atoms, a linear or branched alkenyl group having 2 to 8 carbon atoms or a linear or branched alkynyl group having 2 to 8 carbon atoms, and B represents a hydroxyl group, an oxo group or $=N-OR^6$.

19. The compound of formula (I) according to any one of the above-mentioned 15 to 18 represented by the following formula, a prodrug thereof or a pharmaceutically acceptable salt thereof.

No. 6

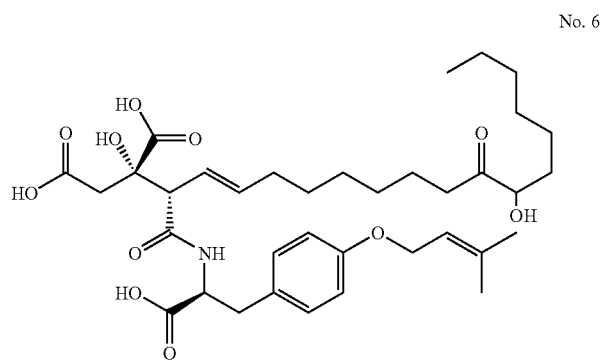

No. 8

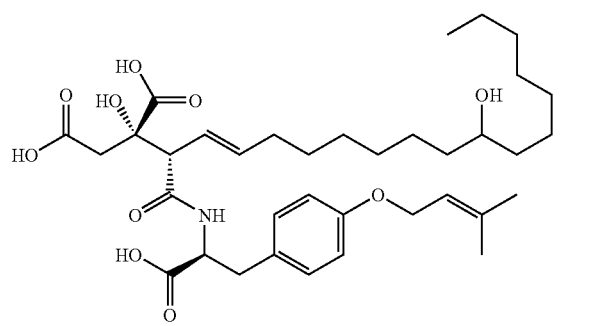

No. 12

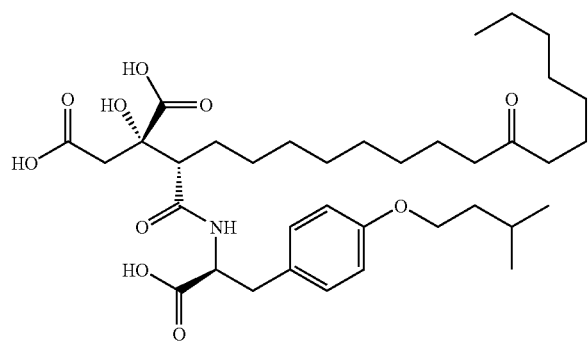

No. 14

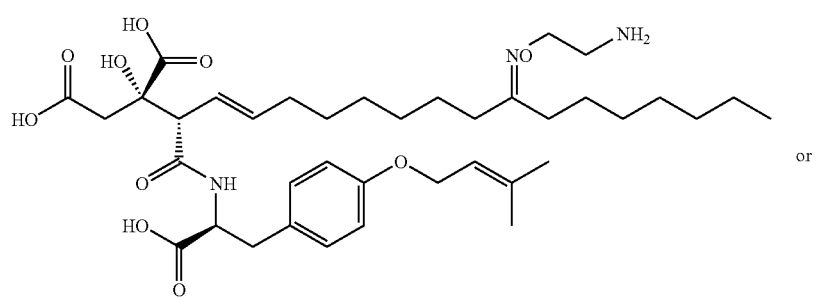

or

-continued

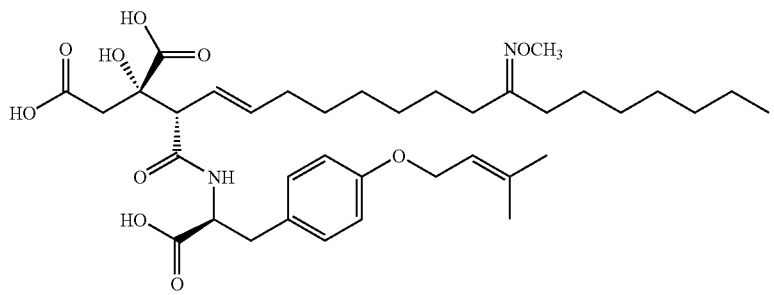

No. 15

20. The compound of formula (I) according to any one of the above-mentioned 15 to 18 represented by the following formula, a prodrug thereof or a pharmaceutically acceptable salt thereof.

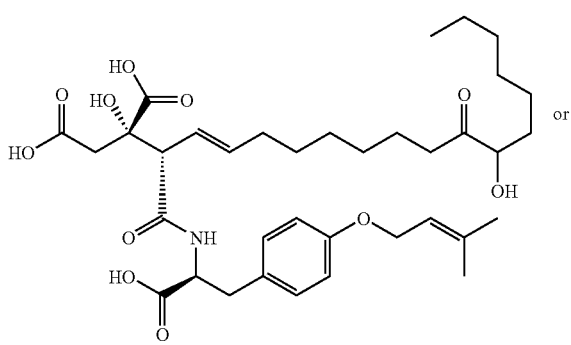

No. 6 or

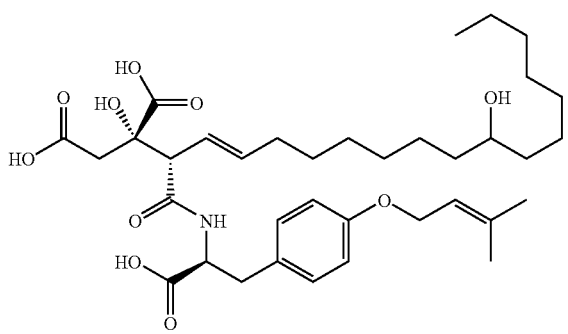

No. 8

21. A pharmaceutical composition comprising a compound of formula (I) according to any one of the above-mentioned 15 to 20, a prodrug thereof or a pharmaceutically acceptable salt thereof.
22. The pharmaceutical composition according to the above-mentioned 21 for preventing or treating viral infectious diseases.
23. The pharmaceutical composition according to the above-mentioned 22, wherein the viral infectious disease is HCV infection.
24. The pharmaceutical composition according to the above-mentioned 23, wherein the HCV infection is hepatitis C.

In the present invention, "linear or branched alkyl group having 1 to 8 carbon atoms" includes for example methyl, ethyl, n-propyl, i-propyl, n-butyl, s-butyl, i-butyl, t-butyl, n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3-ethylbutyl, 2-ethylbutyl, etc.

In the present invention, "linear or branched alkenyl group having 2 to 8 carbon atoms" includes for example 1-propenyl, 2-propenyl(allyl), propen-2-yl, 3-butenyl(homoallyl), 2-isopentenyl, etc.

In the present invention, "linear or branched alkynyl group having 2 to 8 carbon atoms" includes for example 1-propynyl, 1-butynyl, 2-butynyl, etc.

In the present invention, "halogen atom" means a fluorine atom, a chlorine atom, a bromine atom or an iodine atom.

In the present invention, "linear or branched alkyl group having 1 to 6 carbon atoms" includes for example methyl, ethyl, n-propyl, i-propyl, n-butyl, s-butyl, i-butyl, t-butyl, n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3-ethylbutyl, 2-ethylbutyl, etc.

In the present invention, "linear or branched alkenyl group having 2 to 6 carbon atoms" includes for example ethenyl (vinyl), 1-propenyl, 2-propenyl(allyl), propen-2-yl, 3-butenyl(homoallyl), 2-isopentenyl, etc.

In the present invention, "linear or branched alkynyl group having 2 to 6 carbon atoms" includes for example ethynyl, 1-propynyl, 2-propynyl, 1-butynyl, 2-butynyl, 3-butynyl, etc.

In the present invention, "linear or branched alkyl group having 1 to 4 carbon atoms" includes for example, methyl, ethyl, n-propyl, i-propyl, n-butyl, s-butyl, i-butyl, t-butyl, etc.

In the present invention, "linear or branched alkenyl group having 2 to 4 carbon atoms" includes for example ethenyl (vinyl), 1-propenyl, 2-propenyl(allyl), propen-2-yl, 3-butenyl(homoallyl), etc.

In the present invention, "linear branched alkynyl group having 2 to 4 carbon atoms" includes for example 1-propynyl, 1-butynyl, 2-butynyl, etc.

The aforementioned Compound No. 1 is disclosed in International Patent Laid-Open Publication No. WO98/56755, and is known to be derived from microorganisms belonging to the genus *Aureobasidium*, have antimicrobial activity against pathogenic fungi such as *Candida albicans* and *Cryptococcus neoformans*, and have effects that inhibit immune reactions. The aforementioned Compound No. 9 is disclosed in International Patent Laid-Open Publication No. WO94/18157, and is known to be useful as a squalene synthesis inhibitor and antifungal agent.

Production Method of Compounds of the Present Invention: This Compound No. 1 can be produced by culturing a strain of filamentous fungi belonging to the genus *Fusarium* or *Aureobasidium* and so forth that produces the aforementioned compound, followed by isolating from the culture of the above strain.

Moreover, the compounds represented by general formulas (I) and (I') can be obtained with the methods described below using the aforementioned Compound No. 1 as the starting substance.

Production Method 1: A dihydro form (E=single bond, e.g., Compound No. 7) can be obtained by hydrogenating the aforementioned Compound No. 1 in a solvent such as methanol, ethanol, ethyl acetate or tetrahydrofuran, in the presence of a catalyst such as palladium carbon, palladium hydroxide or Raney nickel, at room temperature or while heating.

Production Method 2: An alcohol form (B=hydroxyl group, e.g., Compound No. 8) can be obtained by reducing the aforementioned Compound No. 1 in a solvent such as methanol, ethanol, propanol or tetrahydrofuran, in the presence of a reducing agent such as sodium borohydride, sodium trimethoxyborohydride, sodium cyanoborohydride, lithium borohydride, sodium diethylaluminum hydride or lithium aluminum hydride, at room temperature or while cooling.

Production Method 3: A dealkylated form (X=hydrogen, e.g., Compound No. 9) can be obtained by treating the aforementioned Compound No. 1 in a solvent such as methanol, dioxane, tetrahydrofuran or water, in the presence of hydrochloric acid, sulfuric acid, methanesulfonic acid, trifluoroacetic acid or the like, at room temperature or while cooling. Moreover, a dihydro form (E=single bond and X=hydrogen, e.g., Compound No. 10) can be obtained by hydrogenating the aforementioned Compound No. 9 in a solvent such as methanol, ethanol, ethyl acetate or tetrahydrofuran, in the presence of a catalyst such as palladium carbon, palladium hydroxide, Raney nickel or platinum oxide, at room temperature or while heating.

Production Method 4: A tetraalkyl, tetraalkynyl or tetraalkenyl form (X=Z=alkyl, alkynyl or alkenyl) can be synthesized by treating the aforementioned Compound No. 9 with an alkylating agent such as alkyl halide, allyl halide or alkynyl halide in the presence of base such as sodium hydroxide, potassium hydroxide, calcium carbonate or potassium carbonate, in a solvent such as dimethylformamide (DMF) or tetrahydrofuran at room temperature or while heating. In addition, an alkyl, alkynyl or alkenyl form (X=alkyl, alkynyl or alkenyl, e.g., Compound 16, 17, 18, 19 or 20) can be synthesized by treating this compound in the presence of a base such as sodium hydroxide, potassium hydroxide, calcium carbonate or potassium carbonate, in a solvent such as methanol, dioxane, tetrahydrofuran or water, at room temperature or while heating.

Production Method 5: The aforementioned Compound No. 1 and various amines are treated with a condensation agent such as dicyclohexylcarbodiimide (DCC), water-soluble carbodiimide hydrochloride (WSC.HCl) or 1-hydroxybenzotriazole (HOBt) in a solvent such as dimethylformamide (DMF) or tetrahydrofuran, in the presence of a base such as diisopropylethylamine or triethylamine, at room temperature or while heating to obtain the corresponding triamide form ($R^1$=$R^2$=$R^3$=amino group, e.g., Compound No. 11).

Production Method 6: A tetrahydro form (E=single bond and X=branched alkyl, e.g., Compound No. 12) can be obtained by hydrogenating the aforementioned Compound No. 1 in a solvent such as methanol, ethanol, ethyl acetate or tetrahydrofuran, in the presence of a catalyst such as palladium carbon, palladium hydroxide, Raney nickel or platinum oxide, at room temperature or while heating.

Production Method 7: The aforementioned Compound No. 1 is reacted with various alcohols (R—OH) using a condensation agent such as dicyclohexylcarbodiimide (DCC) in a solvent such as tetrahydrofuran, DMF or dichloromethane at room temperature or while heating to obtain the corresponding triester ($R^1$=$R^2$=$R^3$=R). Alternatively, a trimethyl ester form ($R^1$=$R^2$=$R^3$=$CH_3$) can be obtained by treating the aforementioned Compound No. 1 with an amidodihydro form of trimethylsilyl-diazomethane ($TMSCHN_2$) and so forth in a mixed solvent such as methanol and dichloromethane.

Production Method 8: A de-keto form (B=hydrogen, e.g., Compound No. 13) can be obtained by treating the trimethyl ester form obtained in Production Method 7 with a hydrazine derivative such as 4-toluenesulfonylhydrazide in a solvent such as methanol, ethanol or butanol at room temperature or while heating to obtain the corresponding hydrazide form, and then treating this hydrazide form with a reducing agent such as catecholborane followed by placing in the presence of a base such as lithium hydroxide, sodium hydroxide or potassium hydroxide in a solvent such as ethanol, methanol or water at room temperature or while heating.

Production Method 9: The aforementioned Compound No. 1 and hydroxylamine or various O-substituted hydroxylamines are treated in the presence of pyridine, triethylamine or diisopropylethylamine at room temperature or while heating to obtain the corresponding oxime ether and oxime forms (B=N—$OR^6$ and N—OH, e.g., Compounds Nos. 14 and 15).

Production Method 10: A halide form (B=fluorine) can be obtained by treating the aforementioned Compound No. 1 with diethylaminosulfurtrifluoride (DAST) and so forth in a solvent such as tetrahydrofuran, dichloromethane or chloroform.

Production Method 11: The aforementioned Compound No. 1 and various amines were subjected to reductive amination by treating with a reducing agent such as sodium cyanoborohydride or sodium triacetoxyborohydride in a solvent such as ethanol, methanol or tetrahydrofuran, under neutral or weakly acidic conditions, at room temperature or while heating to obtain the corresponding amine form (B=N($R^4$)($R^5$))

Production Method of Compounds of the Present Invention

There are no particular restrictions on the microbial strains that can be used for production of Compound No. 1, for example, provided they belong to the filamentous fungi such as the genus *Fusarium* and *Aureobasidium*, and are capable of producing the aforementioned compound, examples of which include *Fusarium* sp. strain F1476 (hereinafter referred to as "strain F1476") and *Aureobasidium* sp. strain TKR2449 (International Patent Laid-Open Publication No. WO98/56755)

Strain F1476 has the characteristic of advantageously producing the aforementioned Compound No. 1. The physiological properties of the above strain F1476 are as follows: growth temperature range: 10 to 30° C., and preferably 20 to 30° C.; growth capability pH range: 3 to 11, and preferably 5 to 7.

Strain F1476 is also indicated as *Fusarium* sp. F1476, and was deposited under the accession number FERM BP-8290 at the International Patent Organism Depositary of the National Institute of Advanced Industrial Science and Technology on Feb. 4, 2003.

In the present invention, in addition to the aforementioned strain F1476, spontaneous or artificial mutants of strain F1476, or other fungi belonging to the filamentous fungi such as *Fusarium* or *Aureobasidium* species that have the production capabilities as well as strain F1476 can also be used.

In the present invention, the aforementioned Compound No. 1 can be obtained in culture by inoculating strain F1476 into medium containing a nutrient source followed by culturing. Examples of nutrient sources include carbon sources such as glucose, fructose, saccharose, starch, dextrin, glycerin, molasses, starch syrup, oils and fats and organic acids.

Among the aforementioned nutrient sources, examples of nitrogen sources include organic and inorganic nitrogen compounds such as soybean powder, cottonseed powder, corn steep liquor, casein, peptones, yeast extract, meat extract, wheat germ, urea, amino acids, and ammonium salts.

Among the aforementioned nutrient sources, examples of salts include inorganic salts such as sodium salts, potassium salts, calcium salts, magnesium salts, and phosphate salts. These may be used alone or in suitable combinations.

The aforementioned nutrient sources can be used alone or in suitable combinations.

Heavy metal salts such as iron salts, copper salts, zinc salts or cobalt salts, vitamins such as biotin and vitamin B1, and organic and inorganic substances that assist the growth of microorganisms and promote the production of the aforementioned Compound No. 1 can be suitably added to the aforementioned nutrient source-containing media as necessary.

In addition to the aforementioned nutrient sources, antifoaming agents, surfactants and so forth such as silicone oil and polyalkylene glycol ether can be added to the aforementioned nutrient source-containing media as necessary.

When culturing microbial strains that produce the aforementioned Compound No. 1 in the aforementioned nutrient source containing-medium, a culturing method such as solid culturing or liquid culturing that is typically used when producing a biologically active substance by culturing microorganisms can be employed.

According to the aforementioned culturing methods, the aforementioned Compound No. 1 accumulates in the culture. In the present invention, Compound No. 1 that has accumulated in the culture can be separated from the culture using known methods, followed by further purification as necessary.

The aforementioned separation can be carried out by extracting the entire culture with a non-hydrophilic organic solvent such as ethyl acetate, butyl acetate, chloroform, butanol or methyl isobutyl ketone. In addition, Compound No. 1 can also be separated by separating the culture into culture broth and mycelium by filtration or centrifugation, followed by separating Compound No. 1 from the culture broth and mycelium, respectively.

In order to separate the aforementioned Compound No. 1 from the separated culture broth described above, a method can be used in which the culture liquid is extracted with a non-hydrophilic organic solvent listed above. In addition, a method can also be employed in which the culture broth is contacted with an absorbent and Compound No. 1 present in the culture liquid is adsorbed onto the absorbent followed by eluting with a solvent.

Examples of the aforementioned absorbent include activated charcoal, powdered cellulose and adsorptive resins. The aforementioned solvents can be used alone or by combining two or more types according to the type, properties and so forth of the absorbent. For example, aqueous solutions of a water-soluble organic solvent such as hydrous acetone and hydrous alcohol may be suitably combined for use as a solvent.

A method can also be employed to separate the aforementioned Compound No. 1 from mycelium separated as described above in which the compound are extracted with a hydrophilic organic solvent such as acetone.

In the present invention, the crude extract of the aforementioned Compound No. 1 that has been separated from a culture in the manner described above can be applied to a step in which it is further purified as necessary.

The aforementioned purification can be carried out by a method ordinarily used in the separation and purification of lipophilic biologically active substances, and examples of such methods include column chromatography and high performance liquid chromatography using a carrier such as silica gel, activated alumina, activated charcoal or adsorptive resin. In the case of employing column chromatography using silica gel as the carrier, examples of eluting solvents include chloroform, ethyl acetate, methanol, acetone and water. These may also be used in a combination of two or more solvents.

In the case of employing the aforementioned high performance liquid chromatography, examples of the carrier include silica gel bonded chemically with octadecyl groups, octyl groups or phenyl groups and so forth, and polystyrene porous polymer gel. Examples of the mobile phase include aqueous solutions of water-soluble organic solvents such as hydrous methanol and hydrous acetonitrile.

The aforementioned Compound No. 1 of the present invention can be used in a drug either as such or in the form of a pharmacologically acceptable salt thereof. There are no particular restrictions on the pharmacologically acceptable salt, and examples include salts of mineral acids such as hydrochloric acid, sulfuric acid, nitric acid, phosphoric acid and hydrobromic acid, salts of organic acids such as acetic acid, tartaric acid, lactic acid, citric acid, fumaric acid, maleic acid, succinic acid, methanesulfonic acid, ethanesulfonic acid, benzenesulfonic acid, toluenesulfonic acid, naphthalenesulfonic acid, and camphorsulfonic acid, and salts of alkali metals or alkaline earth metals such as sodium, potassium and calcium.

While the amount of the active ingredient compound contained in the aforementioned pharmaceutical composition is not subjected to any particular restrictions and is suitably selected over a wide range, it is 0.1 to 99.5% by weight, and preferably 0.5 to 90% by weight.

A compound of the present invention can be formulated using a known auxiliary agent such as vehicle, binder, disintegrating agent, lubricant, corrective, dissolving assistant, suspending agent and coating agent which can be normally used in the formulation technology fields of drugs, according to a conventional method. When forming into the form of tablets, a wide range of known carriers in the field can be used, examples of which include vehicles such as lactose, sucrose, sodium chloride, glucose, urea, starch, calcium carbonate, kaolin, crystalline cellulose and silicic acid; binders such as water, ethanol, propanol, simple syrup, liquid glucose, liquid starch, liquid gelatin, carboxymethyl cellulose, shellac, methyl cellulose, potassium phosphate and polyvinyl pyrrolidone; disintegrating agents such as dry starch, sodium alginate, powdered agar, powdered laminaran, sodium hydrogencarbonate, calcium carbonate, polyoxyethylene sorbitan fatty acid ester, sodium lauryl sulfate, monoglyceride stearate, starch and lactose; disintegration inhibitors such as sucrose, stearine, cocoa butter and hydrogenated oils; absorption promoters such as quaternary ammonium salts and sodium lauryl sulfate; moisture retention agents such as glycerin and starch; absorbents such as starch, lactose, kaolin, bentonite and colloidal silicic acid; and lubricants such as refined talc, stearate salts, powdered boric acid and polyethylene glycol.

Moreover, tablets may be in the form of tablets provided with an ordinary coating as necessary, examples of which include sugar-coated tablets, gelatin-encapsulated tablets, enteric-coated tablets, film-coated tablets, or double-layer tablets and multi-layer tablets. When forming into the form of a pill, a wide range of materials can be used as the carrier that are conventionally known in the field, examples of which include vehicles such as glucose, lactose, cocoa butter, starch, hardened vegetable oil, kaolin and talc; binders such as gum arabic powder, tragacanth powder, gelatin and ethanol; and disintegration agents such as laminaran agar. When forming into the form of a suppository, a wide range of materials can be used as the carrier that are conventionally known in the field, examples of which include polyethylene glycol, cocoa butter, higher alcohols, esters of higher alcohols, gelatin and semi-synthetic glycerides. In the case of preparing in the form of an injection preparation, the liquid and suspending agent are preferably sterilized and made to be isotonic with blood, and when these are formed into the form of liquids, emulsions or suspensions, all materials that are commonly used as diluents in the field can be used, examples of which include water, ethanol, propylene glycol, ethoxyisostearyl alcohol, polyoxyisostearyl alcohol and polyoxyethylene sorbitan fatty acid esters. Furthermore, in this case, adequate amounts of salt, glucose or glycerin may be contained in the pharmaceutical preparation to prepare an isotonic solution, and ordinary dissolution assistants, buffers, analgesics and so forth may also be added. Moreover, colorants, preservatives, fragrances, flavorings, sweeteners and other pharmaceuticals may also be contained as necessary.

The aforementioned pharmaceutical composition is preferably administered in the unit dosage form, and can be administered by oral administration, tissue administration (subcutaneous administration, intramuscular administration, intravenous administration, etc.), local administration (percutaneous administration, etc.) or administered rectally. The aforementioned pharmaceutical composition is naturally administered in a dosage form that is suitable for these administration methods.

In the case of administering a compound of the present invention or a pharmaceutically acceptable salt thereof in the form of a medicament, although preferably adjusted in consideration of factors relating to patient status such as age and body weight, administration route, nature and severity of the illness and so forth, the human adult dosage when used as an antiviral drug is normally within the range of 1 to 2000 mg per day as the amount of active ingredient of the present invention. Although there are cases in which a dosage less than the aforementioned range may still be adequate, there are also cases in which conversely a dosage beyond the aforementioned range may be necessary. When administering in large doses, it is preferable to administer by dividing the dosage among several administrations per day.

The aforementioned oral administration can be performed in dose units of a solid, powder or liquid, and can be performed in the form of a powder, granules, tablets, sugar-coated preparations, capsules, drops, sublingual preparations and other dosage forms.

The aforementioned tissue administration can be performed by using the liquid dose unit form for subcutaneous, intramuscular or intravenous injection of a solution or suspension and so forth. These are produced by suspending or dissolving a predetermined amount of a compound of the present invention or pharmaceutically acceptable salt thereof in a non-toxic liquid carrier compatible with the purpose of injection such as an aqueous or oily medium, followed by sterilization of the aforementioned suspension or solution.

The aforementioned local administration (percutaneous administration, etc.) can be performed by using the form of an external preparation such as a liquid, cream, powder, paste, gel or ointment. These can be produced by combining a predetermined amount of a compound of the present invention or pharmaceutically acceptable salt thereof with one or more types of a fragrance, colorant, filler, surfactant, moisture retention agent, skin softener, gelling agent, carrier, preservative or stabilizer and so forth that is applicable to the purpose of the external preparation.

The aforementioned rectal administration can be performed by using a suppository and so forth containing a predetermined amount of a compound of the present invention or pharmaceutically acceptable salt thereof in a low melting point solid composed of, for example, a higher ester such as palmitic myristyl ester, polyethylene glycol, cocoa butter or mixture thereof.

The aforementioned administration can be performed by using the liquid dose unit form for subcutaneous, intramuscular or intravenous injection of a solution or suspension and so forth. These are produced by suspending or dissolving a predetermined amount of a compound of the present invention or pharmaceutically acceptable salt thereof in a non-toxic liquid carrier applicable to the purpose of injection such as an aqueous or oily medium, followed by sterilization of the aforementioned suspension or solution.

EXAMPLES

Although the following provides a detailed explanation of the present invention by indicating examples thereof, the present invention is not limited to these examples.

Example 1

Strain F1476 used in the present invention is a filamentous fungi that was isolated by washing and filtration on Feb. 29, 2000 from fallen leaves collected at the southern slope of Kamakurayama in Kamakura, Japan on Jan. 24, 2000.

Culturing Properties

Growth on potato dextrose agar (PDA) is slow, the organisms reach a diameter of 12 mm after 10 days of irradiation with near ultraviolet light at 25° C., the growth rate is 1.5 to 1.6 mm per day, the organisms form dense mycelial flora, the surfaces are undulated and raised, moist conidiospore bases gather in the center, prominently flocculated clumps of hypha are occasionally formed on the periphery, the color is light orange (apricot, Light orange, Light Apricot to Apricot, Munsell 5YR7/6 to 7/10, Metuen 6A6 to 6B8), and the back surface color ranges from light orange to orange (light orange, bright reddish orange, Tiger Lily, Munsell 5-10YR7/10, Metuen 6B8 to 8A6).

The growth rate is slightly poor in dark, being 0.9 to 1.1 mm per day, the color is lighter and beige (pale beige, Ivory, Munsell 10YR9/2, Metuen 4A3), and the back surface color is light reddish yellow (light reddish yellow, Naples Yellow). However, the color of the hypha is occasionally darker, ranging from ocher to grayish brown (gold, Golden Ocher, light grayish brown, Blond, Munsell 10YR5/4-8, Metuen 5E5-8). In this case, the back surface color is dark yellowish brown (chestnut, dark yellowish brown, Burnt Umber, Munsell 10YR3/6).

Growth on malt extract agar medium (MA) is slow, the organisms reach a diameter of 11 mm after 11 days of irradiation with near ultraviolet light, the growth rate is 1.0 mm/day, dense mycelial flora are formed, the surface is raised and exhibits a wooly or felt texture, the color is light orange (light orange, Light Apricot, Munsell 5YR8/6, Metuen 6A6), and the back surface color is bright orange (bright orange, Nasturtium Orange, Munsell 5YR7/12, Metuen 6A7). The color is paler in dark.

Growth on oatmeal extract agar medium (OA) is rapid, the organisms reach a diameter of 21 mm after 10 days of irradiation with near ultraviolet light, the growth rate is 3.7 mm per day, the organisms are flat and a large number of conidiospore bases are densely concentrated in the center resulting in a granular appearance. The color is light yellowish orange (light yellowish orange, Maize, Munsell 5YR7/8, Metuen 6B6), and the back surface color is the same. The color is paler in dark.

Growth on synthetic nutrient agar medium (SNA) is slow, the organisms reach a diameter of 13 mm after 7 days of irradiation with near ultraviolet light, the growth rate is 1.6 mm per day, the organisms form flat, thin colonies having a felt or wooly texture, moist conidiospore bases are sporadically present in the center, the color is beige (pale beige, Ivory, Munsell 10YR9/2, Metuen 4A3), and the back surface color is the same. Similar growth is observed in dark.

Growth on Miura medium (LCA) is rapid, the organisms reach a diameter of 25 mm after 10 days of irradiation with near ultraviolet light, the growth rate is 3.4 mm per day, the organism forms flat, thin colonies having a granular or cotton texture, moist conidiospore bases are sporadically present in the center, the color is beige (pale beige, Ivory, Munsell 10YR9/2, Metuen 4A3), and the back surface color is the same. Similar growth is observed in dark.

The growth temperature range is 10 to 30° C., and the optimum growth temperature is 20 to 30° C.

The growth pH range is 3 to 11, and the optimum pH is 5 to 7.

Morphological Properties

On SNA, conidiospores shafts rise vertically primarily from airborne mycelia, they are branched, and phialides verticillate directly on the branches or conidiospores shafts resulting in the formation of a complex conidiospores structure. Phialides occasionally grow independently on airborne hypha. Conidiospore structure is formed from hypha lying on the surface of the agar, and some of these do not rise into the air. The conidiospores shafts are 10 to 30 µm long. The phialides are cylindrical and usually have a prominent cup structure on their ends, the size of this structure being from 4.0 to 20.0×2.5 to 3.0 µm. Phialoconidiospores are formed aggregated into a clump with a viscous liquid on the ends of the phialides, they typically have a crescent shape, and have well-defined podocytes at the base. Apical cells are long and narrow or occasionally have a rounded end. They are normally curved and occasionally have an elliptical shape or cylindrical shape, 1-3(4) septa, and measure 6.8 to 30.0×1.9 to 4.9 µm, L/W 3.7 to 8.1 (average: 19.3×3.8 µm), L/W 5.2) Chlamydospores are not observed.

Identification

The complex, cluster-like conidiospore structure formed from light-colored hypha occasionally form conidiospore bases, and the conidiospores are of the phialo type that grow endogenously from the ends of cylindrical phialides, are light-colored, and are composed of 2 to 5 cells having a characteristic vessel or crescent shape. On the basis of the aforementioned morphological characteristics, this strain F1476 is determined to belong to the genus *Fusarium*, an imperfect fungus. Therefore, this fungus was identified as *Fusarium* sp. strain F1476.

REFERENCES

Gerlach, W. and Nirenberg, H. 1982 The genus *Fusarium*—a pictorial atlas. Mitt. Biol. Bundesanst. Land- u. Forstwirtsch. Berlin-Dahlem 209:1-406.

Booth, C. 1971. The genus *Fusarium*. CMI, Kew, Surrey, 237 pp.

Carmichael, J. W., Kendrich, B., Conners, I. L. and Sigler, L. 1980. Genera of Hyphomycetes. University of Alberta Press, Edmonton.

Gams, W. 1971. *Cephalosporium*-artige Schimmelpilze (Hyphomycetes) Gustav Fischer Verlag, Stuttgart. 262 pp.

Example 2

One loopful of microorganisms obtained from a slant culture of strain F1476 was inoculated into 25 500 ml-Erlenmeyer flasks with baffles containing 100 mL of liquid media (2% glucose, 1.5% glycerol, 1% potato starch, 0.25% polypeptone, 0.35% yeast extract, 0.5% calcium carbonate, 0.3% sodium chloride, 0.005% zinc sulfate heptahydrate, 0.0005% copper sulfate pentahydrate, 0.0005% manganese sulfate tetrahydrate and 1% toasted soya), followed by shake culturing at 25° C. for 3 days (shaking rate: 220 rpm) to obtain an inoculated culture seed. 16 mL of this inoculated culture seed was inoculated into 125 500 ml-Erlenmeyer flasks with baffles containing solid media (40 g pressed barley, 24 mL SF1 solution (0.1% yeast extract, 0.05% sodium tartrate, 0.05% potassium dihydrogen phosphate)), followed by stationary culturing at 25° C. for 11 days. 12.5 L of n-butanol was then added to the culture cultured in this manner followed by allowing to stand overnight and then filtering to obtain an n-butanol extract. After concentrating the extract obtained in this manner, it was suspended in 1 L of water, and after adjusting the pH to 2 with hydrochloric acid, it was extracted with 1.1 L of ethyl acetate. The aqueous layer was extracted again with 1.1 L of ethyl acetate and combined with the first extract. 0.9 L of water was then added to this ethyl acetate extract (2.2 L) and then distributed after adjusting the pH to 10 with aqueous sodium hydroxide solution. 1 L of ethyl acetate was again added to the resulting aqueous layer and then extracted after adjusting the pH to 3 with hydrochloric acid. The resulting aqueous layer was again extracted with 1 L of ethyl acetate. The ethyl acetate extract (2 L) thus obtained was then dried over sodium sulfate followed by concentrating and drying to obtain 567 mg of crude extract. This was then dissolved in methanol and repeatedly subjected to preparative high performance liquid chromatography under Conditions 1 indicated below to obtain a fraction containing Compound 1 (Fraction 1), a fraction containing Compounds 2 and 3 (Fraction 2) and a fraction containing Compounds 4, 5 and 6 (Fraction 3). Fraction 1 was concentrated under reduced pressure to obtain 380 mg of Compound 1 in the form of a white powder.

Conditions 1 of High Performance Liquid Chromatography

Instrument: CCPP-D, MCPD-3600 System (Tosoh)

Column: CAPCELL PAK C18 (UG 80, 20 mm×250 mm) (Shiseido)

Mobile phase: Solvent gradient elution using water containing 0.01% trifluoroacetic acid and acetonitrile containing 0.01% trifluoroacetic acid (15% acetonitrile to 98% acetonitrile, stepwise)

Physicochemical Properties of Compound 1

Molecular weight: 659

FAB-MS (positive mode, matrix m-NBA) 660(M+H$^+$)

FAB-MS (negative mode, matrix m-NBA) 658(M−H$^-$)

$^1$H-NMR (in methanol d-4) chemical shift value δ 0.89 (3H, t, J=7 Hz), 1.20-1.40 (14H, m), 1.53(4H, m), 1.73 (3H, s), 1.77 (3H, s), 1.96 (2H, m), 2.42 (4H, m), 2.57 (1H, d, J=16.5 Hz), 2.89 (1H, d, J=16.5 Hz), 2.91 (1H, dd, J=14, 9 Hz), 3.15 (1H, dd, J=14, 4.5 Hz), 3.20 (1H, d, J=8 Hz), 4.47

(2H, d, J=6 Hz), 4.63 (1H, dd, J=9, 4.5 Hz), 5.43 (1H, m), 5.52 (2H, m), 6.78 (2H, d, J=9 Hz), 7.10 (2H, d, J=9 Hz)

Example 3

One of the fractions obtained in Example 2 (Fraction 2, 345 mg) was further subjected to preparative high performance liquid chromatography under Conditions 2 indicated below to separate into a fraction containing Compound 2 (Fraction 2-1, 41.4 mg) and a fraction containing Compound 3 (Fraction 2-2, 4.9 mg). Fraction 2-1 was further subjected to preparative high performance liquid chromatography under Conditions 3 shown below to obtain a fraction containing Compound 2. The resulting fraction was concentrated under reduced pressure to obtain 29.5 mg of Compound 2 in the form of a white powder. Similarly, Fraction 2-2 was subjected to preparative high performance liquid chromatography under Conditions 4 to obtain 3 mg of Compound 3 in the form of a white powder.

Conditions 2 of High Performance Liquid Chromatography

Instrument: CCPP-D, MCPD-3600 System (Tosoh)

Column: CAPCELL PAK C18 (UG 80, 20 mm×250 mm) (Shiseido)

Mobile phase: Solvent gradient elution using water containing 0.01% trifluoroacetic acid and acetonitrile containing 0.01% trifluoroacetic acid (65% acetonitrile to 98% acetonitrile, stepwise)

Conditions 3 of High Performance Liquid Chromatography

Instrument: CCPP-D, MCPD-3600 System (Tosoh)

Column: CAPCELL PAK Speriorex ODS (20 mm×250 mm) (Shiseido)

Mobile phase: Solvent gradient elution using water containing 0.01% trifluoroacetic acid and acetonitrile containing 0.01% trifluoroacetic acid (65% acetonitrile to 98% acetonitrile, stepwise)

Conditions 4 of High Performance Liquid Chromatography

Instrument: CCPP-D, MCPD-3600 System (Tosoh)

Column: CAPCELL PAK C8 (SG 120, 20 mm×250 mm) (Shiseido)

Mobile phase: Solvent gradient elution using water containing 0.01% trifluoroacetic acid and acetonitrile containing 0.01% trifluoroacetic acid (65% acetonitrile to 98% acetonitrile, stepwise)

Physicochemical Properties of Compound 2

Molecular weight: 673

ESI (LC/MS positive mode) 674 (M+H$^+$)

$^1$H-NMR (in methanol d-4) chemical shift value δ 0.89 (3H, t, J=7 Hz), 1.20-1.40 (14H, m), 1.53 (4H, m), 1.73 (3H, s), 1.77 (3H, s), 1.96 (2H, m), 2.42 (4H, m), 2.59 (1H, d, J=16.5 Hz), 2.89 (1H, d, J=16.5 Hz), 2.91 (1H, dd, J=14, 9 Hz), 3.15 (1H, dd, J=14, 4.5 Hz), 3.20 (1H, d, J=8 Hz), 3.63 (3H, s), 4.47 (2H, d, J=6 Hz), 4.63 (1H, dd, J=9, 4.5 Hz), 5.43 (1H, m), 5.54 (2H, m), 6.78 (2H, d, J=9 Hz), 7.10 (2H, d, J=9 Hz)

Physicochemical Properties of Compound 3

Molecular weight: 687

ESI (LC/MS positive mode) 688 (M+H$^+$)

$^1$H-NMR (in methanol d-4) chemical shift value δ 0.89 (3H, t, J=7 Hz), 1.20-1.40 (14H, m), 1.53 (4H, m), 1.73 (3H, s), 1.77 (3H, s), 1.96 (2H, m), 2.42 (4H, m), 2.56 (1H, d, J=16.5 Hz), 2.89 (1H, d, J=16.5 Hz), 2.91 (1H, dd, J=14 Hz, 9 Hz), 3.11 (1H, dd, J=14, 4.5 Hz), 3.20 (1H, d, J=8 Hz), 3.63 (3H, s), 3.71 (3H, s), 4.47 (2H, d, J=6 Hz), 4.64 (1H, dd, J=9, 4.5 Hz), 5.43 (1H, m), 5.54 (2H, m), 6.79 (2H, d, J=9 Hz), 7.08 (2H, d, J=9 Hz)

Example 4

One of the fractions obtained in Example 2 (Fraction 3, 453 mg) was further subjected to preparative high performance liquid chromatography under the aforementioned Conditions 2 to separate into a fraction containing Compound 4 (Fraction 3-1), a fraction containing Compound 5 (Fraction 3-2, 16.4 mg) and a fraction containing Compound 6 (Fraction 3-3, 26.5 mg). Fraction 3-1 was concentrated under reduced pressure to obtain 2 mg of Compound 4 in the form of a white powder. Fraction 3-2 was further subjected to preparative high performance liquid chromatography under Conditions 5 shown below to obtain a fraction containing Compound 5. The resulting fraction was concentrated under reduced pressure to isolate 4 mg of Compound 5 in the form of a white powder. Similarly, Fraction 3-3 was subjected to preparative high performance liquid chromatography under Conditions 5 to obtain 6 mg of Compound 6 in the form of a white powder.

Conditions 5 of High Performance Liquid Chromatography

Instrument: CCPP-D, MCPD-3600 System (Tosoh)

Column: CAPCELL PAK C18 (UG 80, 20 mm×250 mm) (Shiseido)

Mobile phase: Solvent gradient elution using water containing 0.01% trifluoroacetic acid and acetonitrile containing 0.01% trifluoroacetic acid (50% acetonitrile to 98% acetonitrile, stepwise)

Physicochemical Properties of Compound 4

Molecular weight: 607

ESI (LC/MS positive mode) 608 (M+H$^+$)

$^1$H-NMR (in methanol d-4) chemical shift value δ 0.89 (3H, t, J=7 Hz), 1.20-1.40 (14H, m), 1.58 (4H, m), 2.00 (2H, m), 2.52 (2H, m), 2.56 (1H, d, J=16 Hz), 2.88 (1H, dd, J=14, 8 Hz), 2.90 (1H, d, J=16 Hz), 3.10 (1H, dd, J=14, 4 Hz), 3.20 (1H, d, J=8 Hz), 4.05 (1H, dd, J=8, 4.5 Hz) 4.60 (1H, dd, J=8, 4.5 Hz), 5.53 (2H, m), 6.67 (2H, d, J=8 Hz), 7.02 (2H, d, J=8 Hz)

Physicochemical Properties of Compound 5

Molecular weight: 614

ESI (LC/MS positive mode) 615 (M+H$^+$)

$^1$H-NMR (in methanol d-4) chemical shift value δ 0.89 (3H, t, J=7 Hz), 1.20-1.40 (14H, m), 1.53 (4H, m), 1.93 (2H, m), 2.27 (4H, m), 2.58 (1H, d, J=16 Hz), 2.86 (1H, d, J=16 Hz), 3.22 (2H, m), 3.65 (1H, d, J=9 Hz), 4.73 (1H, dd, J=8, 5 Hz), 5.50 (2H, m), 6.96 (1H, t, J=7 Hz), 7.06 (1H, t, J=7 Hz), 7.10 (1H, s), 7.29 (1H, d, J=7 Hz) 7.55 (1H, d, J=7 Hz)

Physicochemical Properties of Compound 6

Molecular weight: 675

ESI (LC/MS positive mode) 676 (M+H$^+$)

$^1$H-NMR (in methanol d-4) chemical shift value δ 0.89 (3H, t, J=7 Hz), 1.20-1.40 (14H, m), 1.53 (4H, m), 1.72 (3H, s), 1.77 (3H, s), 1.92 (2H, m), 2.42 (2H, m), 2.57 (1H, d, J=16 Hz), 2.89 (1H, d, J=16 Hz), 2.91 (1H, dd, J=14, 9 Hz), 3.15 (1H, dd, J=14, 4.5 Hz), 3.20 (1H, d, J=7 Hz), 4.05 (1H, dd, J=8, 4 Hz), 4.47 (2H, d, J=6 Hz), 4.62 (1H, dd, J=9, 4.5 Hz), 5.43 (1H, m), 5.52 (2H, m), 6.78 (2H, d, J=9 Hz), 7.10 (2H, d, J=9 Hz)

Example 5

Synthesis of Compound 7

10% Pd—C (1 mg) was added to a methanol solution (2 mL) of Compound 1 (5 mg, 0.0075 mmol) and stirred at room temperature for 24 hours in a hydrogen gas atmosphere. The palladium catalyst was then filtered out followed by concentration of the filtrate under reduced pressure. The resulting residue was purified by preparative high performance liquid chromatography under the conditions indicated below to obtain Compound 7 (1.7 mg, 34%) in the form of a colorless oily substance.

Conditions of High Performance Liquid Chromatography
Instrument: CCPS, MCPD-3600 System (Tosoh)
Column: CAPCELL PAK C18 (UG, 4.6 mm×150 mm) (Shiseido)
Mobile phase: Solvent gradient elution using water containing 0.005% trifluoroacetic acid and acetonitrile containing 0.005% trifluoroacetic acid (65% acetonitrile to 98% acetonitrile, stepwise)
Physicochemical Properties of Compound 7
Molecular weight: 661
ESI (LC/MS positive mode) 662 (M+H$^+$)
$^1$H-NMR (in methanol d-4) chemical shift value δ: 0.89 (3H, t, J=7 Hz), 0.96 (6H, d, J=6.5 Hz), 1.20-1.35 (14H, m), 1.46-1.58 (4H, m), 1.64 (2H, q, J=6.5 Hz), 1.83 (1H, quintet, J=6.5 Hz), 1.93-2.01 (2H, m), 2.43 (4H, t, J=7.5 Hz), 2.58 (1H, d, J=16 Hz), 2.89 (1H, d, J=16 Hz), 2.91 (1H, dd, J=14, 9 Hz), 3.16 (1H, dd, J=14, 5 Hz), 3.19 (1H, d, J=8.5 Hz), 3.95 (2H, t, J=6.5 Hz), 4.64 (1H, dd, J=9, 5 Hz), 5.50-5.56 (2H, m), 6.79 (2H, d, J=8.5 Hz), 7.11 (2H, d, J=8.5 Hz)

Example 6

Synthesis of Compound 8
Sodium borohydride (13 mg, 0.33 mmol) was added to a methanol solution (1.5 mL) of Compound 1 (22 mg, 0.033 mmol) and stirred at room temperature for 4 hours. The reaction solution was then neutralized with 1 N aqueous hydrochloric acid and the solvent was distilled off under reduced pressure. Dichloromethane (10 ml) was added to the resulting residue and the insoluble matter was filtered out. The filtrate was then applied to Mega Bond Elute Diol (500 mg, Varian) to obtain Compound 8 (11 mg, 51%) in the form of a white powder from the dichloromethane/methanol (30:1) eluate.
Physicochemical Properties of Compound 8
Molecular weight: 661
ESI (LC/MS positive mode) 662 (M+H$^+$)
$^1$H-NMR (in methanol d-4) chemical shift value δ: 0.90 (3H, t, J=7 Hz), 1.20-1.48 (22H, m), 1.73 (3H, s), 1.77 (3H, s), 1.93-2.04 (2H, m), 2.58 (1H, d, J=16 Hz), 2.89 (1H, d, J=16 Hz), 2.91 (1H, dd, J=14, 9 Hz), 3.16 (1H, dd, J=14, 4.5 Hz), 3.20 (1H, d, J=8 Hz), 3.44-3.53 (1H, m), 4.48 (2H, d, J=6.5 Hz), 4.64 (1H, dd, J=9, 4.5 Hz), 5.41-5.47 (1H, m), 5.51-5.56 (2H, m), 6.79 (2H, d, J=8.5 Hz), 7.11 (2H, d, J=8.5 Hz)

Example 7

Synthesis of Compound 9
Compound 1 (30 mg, 0.045 mmol) was added to a mixed solution of 1,4-dioxane (1 mL) and 6 N aqueous hydrochloric acid (0.5 mL) followed by stirring at 50° C. for 5 minutes and then stirring at room temperature for 4 hours. Water (15 mL) was then added to the reaction liquid followed by a extraction with ethyl acetate (15 mL). After washing with a saturated aqueous NaCl solution (15 mL), the organic layer was dehydrated and dried with anhydrous sodium sulfate. The solvent was then distilled off under reduced pressure to obtain Compound 9 (24 mg, 91%) in the form of a white powder.
Physicochemical Properties of Compound 9
Molecular weight: 591
ESI (LC/MS positive mode) 592 (M+H$^+$)
$^1$H-NMR (in methanol d-4) chemical shift value δ: 0.90 (3H, t, J=7 Hz), 1.20-1.40 (14H, m), 1.46-1.59 (4H, m), 1.93-2.03 (2H, m), 2.43 (4H, t, J=7 Hz), 2.62 (1H, d, J=16 Hz), 2.89 (1H, d, J=14, 9 Hz), 2.91 (1H, d, J=16 Hz), 3.11 (1H, dd, J=14, 5 Hz), 3.21 (1H, d, J=8 Hz), 4.61 (1H, dd, J=9, 5 Hz), 5.46-5.57 (2H, m), 6.67 (2H, d, J=8.5 Hz), 7.02 (2H, d, J=8.5 Hz)

Example 8

Synthesis of Compound 10
10% Pd—C (3 mg) was added to a methanol solution (1 mL) of Compound 9 (12 mg, 0.020 mmol) followed by stirring at room temperature for 3 hours in a hydrogen gas atmosphere. The palladium catalyst was filtered out and the filtrate was concentrated under reduced pressure. The residue was then purified by developing by thin layer chromatography (DIOL F254s, Merck, developing solvent: dichloromethane/methanol (10:1), Rf value: 0.4) to obtain Compound 10 (3 mg, 25%) in the form of a white powder.
Physicochemical Properties of Compound 10
Molecular weight: 593
ESI (LC/MS positive mode) 594 (M+H$^+$)
$^1$H-NMR (in methanol d-4) chemical shift value δ: 0.90 (3H, t, J=7 Hz), 1.03-1.40 (20H, m), 1.45-1.60 (4H, m), 2.40-2.47 (4H, m), 2.54-2.64 (1H, m), 2.65 (1H, d, J=17 Hz), 2.75-2.88 (2H, m), 3.20 (1H, dd, J=14.5, 4.5 Hz), 4.65 (1H, dd, J=10, 4.5 Hz), 6.69 (2H, d, J=8.5 Hz), 7.08 (2H, d, J=8.5 Hz)

Example 9

Synthesis of Compound 11
Ammonium chloride (7.3 mg, 0.136 mmol), water-soluble carbodiimide hydrochloride (WSC HCl, 28 mg, 0.145 mmol), 1-hydroxybenzotriazole (HOBt, 22 mg, 0.145 mmol) and N,N-diisopropylethylamine (DIPEA, 174 μL, 0.145 mmol) were added to a DMF solution (1 mL) of Compound 1 (20 mg, 0.030 mM) followed by stirring at room temperature for 17 hours. After distilling off the solvent under reduced pressure, the residue was dissolved in ethyl acetate (20 mL) followed by washing with saturated aqueous ammonium chloride (20 mL) and saturated aqueous NaCl solution (20 mL). After dehydrating and drying the organic layer with anhydrous sodium sulfate, the solvent was distilled off under reduced pressure. The resulting residue was purified by preparative high performance liquid chromatography under the conditions indicated below to obtain Compound 11 (4.4 mg, 22%) in the form of a white powder.
Conditions of High Performance Liquid Chromatography
Instrument: CCPS, MCPD-3600 System (Tosoh)
Column: CAPCELL PAK C18 (UG, 4.6 mm×150 mm) (Shiseido)
Mobile phase: Solvent gradient elution using water containing 0.005% trifluoroacetic acid and acetonitrile containing 0.005% trifluoroacetic acid (65% acetonitrile to 98% acetonitrile, stepwise)
Physicochemical Properties of Compound 11
Molecular weight: 656
ESI (LC/MS positive mode) 657 (M+H$^+$)
$^1$H-NMR (in methanol d-4) chemical shift value δ: 0.90 (3H, t, J=7 Hz), 1.19-1.39 (14H, m), 1.46-1.59 (4H, m), 1.73 (3H, s), 1.77 (3H, s), 1.88-1.98 (2H, m), 2.28 (1H, d, J=15 Hz), 2.43 (4H, t, J=7.5 Hz), 2.74 (1H, d, J=15 Hz), 2.79 (1H, dd, J=14, 10 Hz), 3.15 (1H, dd, J=14, 4.5 Hz), 3.18 (1H, d, J=8

Hz), 4.47 (2H, d, J=6.5 Hz), 4.59 (1H, dd, J=10, 4.5 Hz), 5.39-5.49 (3H, m), 6.79 (2H, d, J=8.5 Hz), 7.13 (2H, d, J=8.5 Hz)

Example 10

Synthesis of Compound 12

10% Pd—C (10 mg) was added to a methanol solution (10 mL) of Compound 1 (80 mg, 0.12 mmol) followed by stirring at room temperature for 20 hours in a hydrogen gas atmosphere. The palladium catalyst was filtered out using Celite and the filtrate was concentrated under reduced pressure. The residue was then purified by developing by thin layer chromatography (DIOL F254s, Merck, developing solvent: dichloromethane/methanol (10:1), Rf value: 0.8) to obtain Compound 12 (41 mg, 51%) in the form of a white powder.

Physicochemical Properties of Compound 12

Molecular weight: 663

ESI (LC/MS positive mode) 664 (M+H$^+$)

$^1$H-NMR (in methanol d-4) chemical shift value δ: 0.90 (3H, t, J=7 Hz), 0.96 (6H, d, J=6.5 Hz), 1.07-1.35 (20H, m), 1.46-1.56 (4H, m), 1.64 (2H, q, J=6.5 Hz), 1.81 (1H, sexet, J=6.5 Hz), 2.43 (4H, t, J=7.5 Hz), 2.50-2.58 (1H, m), 2.61 (1H, d, J=16.5 Hz), 2.84 (1H, dd, J=14.5, 10.5 Hz), 2.92 (1H, d, J=16.5 Hz), 3.22 (1H, dd, J=14.5, 4 Hz), 3.95 (2H, t, J=6.5 Hz), 4.71 (1H, dd, J=10.5, 4 Hz), 6.81 (2H, d, J=8.5 Hz), 7.16 (2H, d, J=8.5 Hz)

Example 11

Synthesis of Compound 13 a) Synthesis of Trimethyl Ester Derivative of Compound 1

A 10 v/v % hexane solution (4.3 mL) of trimethylsilyl diazomethane was added to a mixed solution of methanol (15 mL) and dichloromethane (15 mL) of Compound 1 (260 mg, 0.39 mmol) followed by stirring at room temperature for 3 hours. The reaction liquid was then concentrated under reduced pressure and the resulting residue was purified with Mega Bond Elute Silica Gel (2 g, Varian). The trimethyl ester form of Compound 1 (230 mg, 83%) was obtained in the form of a white powder from the hexane/ethyl acetate (1:1) eluate.

Physicochemical Properties of Trimethyl ester Form of Compound 1

Molecular weight: 701

FAB-MS (positive mode, matrix m-NBA) 702 (M+H$^+$)

$^1$H-NMR (in methanol d-4) chemical shift value δ: 0.89 (3H, t, J=7 Hz), 1.20-1.37 (14H, m), 1.46-1.59 (4H, m), 1.73 (3H, s), 1.77 (3H, s), 1.93-2.03 (2H, m), 2.43 (4H, t, J=7.5 Hz), 2.60 (1H, d, J=16 Hz), 2.89 (1H, dd, J=14, 9 Hz), 2.93 (1H, d, J=16 Hz), 3.11 (1H, dd, J=14, 5 Hz), 3.19 (1H, d, J=8.5 Hz), 3.63 (3H, s), 3.71 (3H, s), 3.72 (3H, s), 4.48 (2H, d, J=6.5 Hz), 4.63 (1H, dd, J=9, 5 Hz), 5.40-5.58 (3H, m), 6.79 (2H, d, J=8.5 Hz), 7.07 (2H, d, J=8.5 Hz)

b) Synthesis of Hydrazide Derivative

4-Toluenesulfonylhydrazide (6.7 mg, 0.036 mmol) was added to a methanol solution (2 mL) of the aforementioned trimethyl ester form of Compound 1 (21 mg, 0.030 mmol) followed by reflux with heating for 1.5 hours. The solvent was distilled off under reduced pressure, and the resulting residue was dried under reduced pressure for 24 hours. The residue was then dissolved in anhydrous chloroform (2 mL) followed by the addition of 1 M catecholborane tetrahydrofuran solution (75 μL, 0.075 mmol) at 0° C. and stirring at the same temperature for 3 hours. Methanol (20 μL) was added to the reaction liquid followed by stirring at room temperature for 10 minutes. Moreover, sodium acetate (8 mg, 0.060 mmol) and dimethyl sulfoxide (32 μL) were added and refluxed with heating for 1 hour. Water (20 mL) was then added to the reaction liquid followed by extracting twice with ethyl acetate (20 mL). The organic layers were combined, washed with a saturated aqueous NaCl solution (20 mL) and then dehydrated and dried over anhydrous sodium sulfate followed by distilling off the solvent under reduced pressure. The residue was then purified by developing by thin layer chromatography (Silica Gel F254, Merck, developing solvent: hexane/ethyl acetate (3:1), Rf value: 0.3) to obtain the hydrazide form (11 mg, 54%) in the form of a white powder.

Physicochemical Properties of Hydrazide derivative

Molecular weight: 687

FAB-MS (positive mode, matrix m-NBA) 688 (M+H$^+$)

$^1$H-NMR (in deutero chloroform) chemical shift value δ: 0.88 (3H, t, J=6.5 Hz), 1.15-1.37 (24H, m), 1.74 (3H, s), 1.80 (3H, s), 1.94-2.04 (2H, m), 2.62 (1H, d, J=16 Hz), 2.87 (1H, d, J=16 Hz), 3.00 (1H, dd, J=14, 7 Hz), 3.10 (1H, dd, J=14, 5.5 Hz), 3.16 (1H, d, J=9 Hz), 3.67 (3H, s), 3.72 (3H, s), 3.76 (3H, s), 4.47 (2H, d, J=7 Hz), 4.76-4.83 (1H, m), 5.41-5.69 (3H, m), 6.76 (1H, d, J=8 Hz), 6.80 (2H, d, J=9 Hz), 7.03 (2H, d, J=9 Hz)

c) Synthesis of Compound 13

1 M aqueous lithium hydroxide solution (0.15 mL, 0.15 mM) was added to an ethanol solution (1 mL) of the aforementioned hydrazide form (10 mg, 0.015 mmol) followed by stirring at room temperature for 16 hours. The reaction liquid was then neutralized with 1 N aqueous hydrochloric acid solution and the solvent was concentrated under reduced pressure. The residue was then purified by developing by thin layer chromatography (DIOL F254s, Merck, developing solvent: dichloromethane/methanol (10:1), Rf value: 0.5) to obtain Compound 13 (3 mg, 35%) in the form of a white powder. It should be noted that Compound 13 in this example was obtained in the form of a compound in which the configuration of the tyrosine portion is that of a racemer.

Physicochemical Properties of Compound 13

Molecular weight: 645

ESI (LC/MS positive mode) 646 (M+H$^+$)

$^1$H-NMR (in methanol d-4) chemical shift value δ: 0.90 (3H, t, J=7 Hz), 1.18-1.44 (24H, m), 1.73 (3H, s), 1.77 (3H, s), 1.90-2.04 (2H, m), 2.57-2.68 (1H, m), 2.86-3.22 (4H, m), 4.47 (2H, d, J=6.5 Hz), 4.56-4.67 (1H, m), 5.39-5.65 (3H, m), 6.78-6.84 (2H, m), 7.09-7.16 (2H, m)

Example 12

Synthesis of Compound 14

Compound 1 (10 mg, 0.015 mmol) and O-(2-aminoethyl)-hydroxylamine dihydrochloride (4.5 mg, 0.030 mmol) were dissolved in pyridine (0.2 mL) followed by stirring at room temperature for 16 hours. After distilling off the solvent under reduced pressure, the residue was purified by developing by thin layer chromatography (DIOL F254s, Merck, developing solvent: dichloromethane/methanol (5:1), Rf value: 0.5) to obtain Compound 14 (Ro 4575919) (7.7 mg, 71%) in the form of a colorless oily substance.

Physicochemical Properties of Compound 14

Molecular weight: 717

ESI (LC/MS positive mode) 718 (M+H$^+$)

$^1$H-NMR (in methanol d-4) chemical shift value δ: 0.90 (3H, t, J=7 Hz), 1.21-1.40 (14H, m), 1.42-1.56 (4H, m), 1.74 (3H, s), 1.78 (3H, s), 1.88-2.04 (2H, m), 2.18 (2H, t, J=7.5 Hz), 2.30-2.37 (2H, m), 2.63 (1H, d, J=15 Hz), 2.84-2.97 (2H, m), 3.12-3.25 (4H, m), 4.18 (2H, t, J=5 Hz), 4.48 (2H, d, J=6.5

Hz), 4.63 (1H, dd, J=9, 4 Hz), 5.40-5.62 (3H, m), 6.80 (2H, d, J=8.5 Hz), 7.11 (2H, d, J=8.5 Hz)

Example 13

Synthesis of Compound 15

Compound 1 (10 mg, 0.015 mmol) and O-methylhydroxylamine hydrochloride (2.5 mg, 0.030 mmol) were dissolved in pyridine (0.2 mL) followed by stirring at room temperature for 15 hours. After distilling off the solvent under reduced pressure, the residue was purified with Mega Bond Elute Diol (500 mg, Varian). Compound 15 (9.6 mg, 92%) was obtained in the form of a colorless oily substance from the dichloromethane/methanol (25:1) eluate.

Physicochemical Properties of Compound 15

Molecular weight: 688

ESI (LC/MS positive mode) 689 (M+H$^+$)

$^1$H-NMR (in methanol d-4) chemical shift value δ: 0.90 (3H, t, J=7 Hz), 1.20-1.36 (14H, m), 1.40-1.50 (4H, m), 1.74 (3H, s), 1.78 (3H, s), 1.91-2.00 (2H, m), 2.14 (2H, t, J=7.5 Hz), 2.27 (2H, t, J=7.5 Hz), 2.59 (1H, d, J=16 Hz), 2.90 (1H, d, J=16 Hz), 2.91 (1H, dd, J=14, 9 Hz), 3.16 (1H, dd, J=14, 4.5 Hz), 3.20 (1H, d, J=8.5 Hz), 3.75 (3H, s), 4.48 (2H, d, J=6.5 Hz), 4.64 (1H, dd, J=9, 4.5 Hz), 5.41-5.49 (1H, m), 5.52-5.60 (2H, m), 6.80 (2H, d, J=8.5 Hz), 7.11 (2H, d, J=8.5 Hz)

In addition, the following compounds can be synthesized according to methods similar to those described above.

No. 16

No. 17

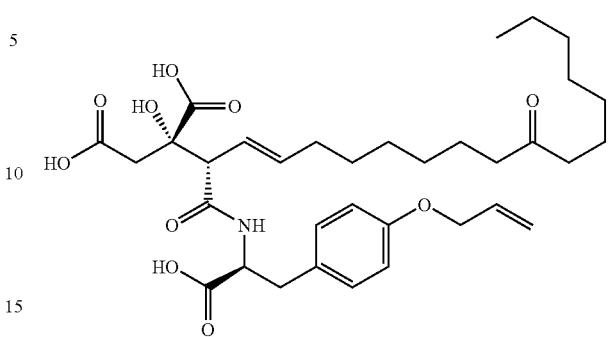

No. 18

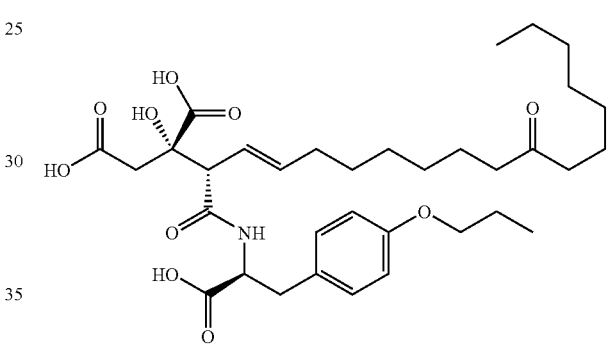

No. 19

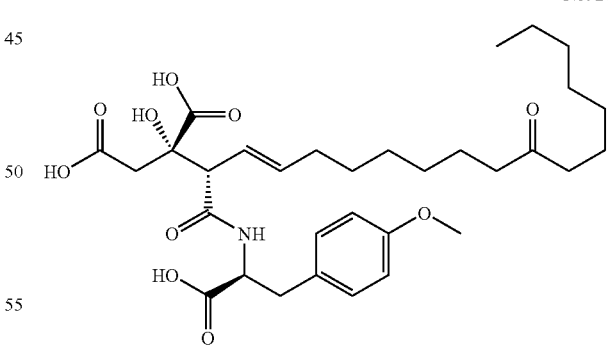

No. 20

Moreover, the production method of the following compound of formula (I) of the present invention and pharmacological activity of the compound of formula (I) will be described by way of Examples.

Example 14

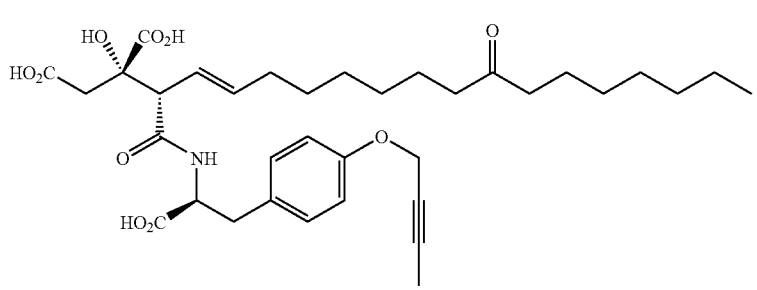

1-1 (Step 1-1)

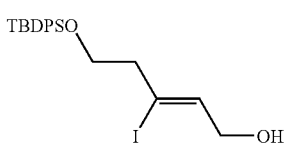

According to the method described in literature (J. Org. Chem. 1989, 45, 5522, B. E. Marron, et al.), compound a (70.1 g) of the formula:

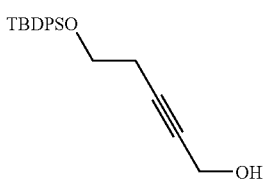

was synthesized and a solution of this compound a in anhydrous diethyl ether (700 ml) was cooled to 0° C., and sodium bis(2-methoxyethoxy)aluminum hydride (414 mmol, 121 ml, 70% toluene solution) was slowly added thereto. The ice bath was removed after 5 minutes of the completion of addition of the reagent and stirring was continued at room temperature for one hour. The reaction mixture was cooled to 0° C. and anhydrous ethyl acetate (19.8 ml, 203 mmol) was slowly added thereto. After the mixture was stirred at the same temperature for 10 minutes, it was cooled to −78° C., followed by addition of iodine (76.1 g, 300 mmol). The temperature of the mixture was gradually raised to room temperature over 2 hours to complete the reaction. An aqueous sodium hydrogensulfite solution was added to the reaction mixture and ethyl acetate was added thereto. After the reaction solution was subjected to suction filtration by selite, an organic layer was separated and an aqueous layer was again extracted with ethyl acetate. After the combined organic layer was dried over anhydrous sodium sulfate, it was concentrated under reduced pressure to obtain a crude title compound (100 g) as a light brown oil. The crude product thus obtained was used as such for the subsequent reaction.

Physicochemical properties of Compound b
Molecular weight 466
FAB-MS (positive mode, matrix m-NBA) 467 (M+H$^+$)
$^1$H-NMR (in deutero chloroform) chemical shift value δ: 1.04 (9H, s), 1.44(1H, t, J=5 Hz), 2.73 (2H, t, J=6 Hz), 3.80 (2H, t, J=6 Hz), 4.18 (2H, t, J=5 Hz), 5.91 (1H, t, J=5 Hz), 7.35-7.46 (6H, m), 7.65-7.69 (4H, m)

1-2 (Step 1-2)

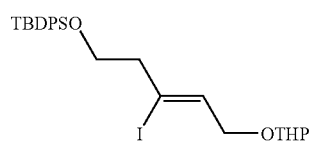

A solution (300 ml) of compound b obtained in the above reaction in dichloromethane was cooled to 0° C. and dihydropyrane (22.7 ml, 248 mmol) was added thereto. Pyridinium paratoluenesulfonate (260 mg, 1 mmol) was added to this solution. After one hour, an aqueous sodium bicarbonate solution was added thereto to stop the reaction. The separated organic layer was washed with a saturated aqueous NaCl solution and dried over anhydrous sodium sulfate, followed by concentration under reduced pressure. The resulting crude compound c (108 g) was used as such for the subsequent reaction.

Physicochemical Properties of Compound c
Molecular weight 550
FAB-MS (positive mode, matrix m-NBA) 551 (M+H$^+$)
$^1$H-NMR (in deutero chloroform) chemical shift value δ: 1.04 (9H, s), 1.49-1.91 (6H, m), 2.74 (2H, t, J=6 Hz), 3.46-3.58 (2H, m), 3.76 (2H, t, J=6 Hz), 3.82-3.93 (1H, m), 4.06 (1H, dd, J=13, 6 Hz), 4.27 (1H, dd, J=13, 6 Hz), 4.65 (1H, t, J=3 Hz), 5.91 (1H, t, J=5 Hz), 7.35-7.43 (6H, m), 7.65-7.69 (4H, m)

1-3 (Step 1-3)

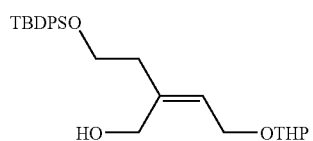

The crude compound c (4.73 g) was dissolved in anhydrous diethyl ether (30 ml) and cooled to −78° C. Tert-butyl lithium (17.2 mmol, 10.7 ml, 1.6N pentane solution) was slowly added thereto. After the mixture was stirred at the same temperature for one hour, para-formaldehyde (18.9 mmol, 570 mg) was added thereto and the mixture was stirred at the same temperature for 30 minutes. The temperature of the mixture was raised to 0° C. and it was stirred for one hour. An aqueous ammonium chloride solution was added thereto to stop the reaction and it was extracted with ethyl acetate. An aqueous layer was extracted with a small amount of ethyl acetate and the combined organic layer was washed with a saturated aqueous NaCl solution, followed by drying over anhydrous sodium sulfate. The crude product obtained by concentration under reduced pressure was purified by column chromatography (silica gel, hexane-ethyl acetate 9:1-4:1) to obtain compound d (1.635 g) as a colorless oil.

Physicochemical Properties of Compound d
Molecular weight 454
FAB-MS (positive mode, matrix m-NBA) 455 (M+H$^+$)
$^1$H-NMR (in deutero chloroform) chemical shift value δ: 1.04 (9H, s), 1.49-1.89 (6H, m), 2.41 (2H, t, J=6 Hz), 3.03 (1H, t, J=6 Hz), 3.47-3.58 (2H, m), 3.75-3.92 (3H, m), 4.08-4.26 (4H, m), 4.68 (1H, t, J=3 Hz), 5.53 (1H, t, J=7 Hz), 7.35-7.47 (6H, m), 7.64-7.68 (4H, m)

1-4 (Step 1-4)

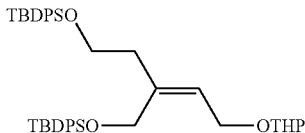

e

A solution (2 ml) of compound d (344 mg, 0.76 mmol) and imidazole (77 mg, 1.14 mmol) in anhydrous N,N-dimethylformamide was cooled to 0° C. and tert-butyldiphenylchlorosilane (0.2 ml, 0.76 mmol) was added thereto, followed by stirring of the mixture for 2 hours. An aqueous ammonium chloride solution was added thereto to stop the reaction and the reaction mixture was extracted with hexane. The organic layer was washed twice with water, then a saturated aqueous NaCl solution and dried over anhydrous sodium sulfate. It was concentrated under reduced pressure to obtain a crude compound e (554 mg) as a colorless oil.

Physicochemical Properties of Compound e
Molecular weight 692
FAB-MS (positive mode, matrix m-NBA) 715 (M+Na$^+$)
$^1$H-NMR (in deutero chloroform) chemical shift value δ: 1.00 (9H, s), 1.04 (9H, s), 1.38-1.82 (6H, m), 2.49 (2H, t, J=7 Hz), 3.29-3.42 (1H, m), 3.63-3.85 (4H, m), 4.00-4.09 (1H, m), 4.14 (2H, s), 4.46 (1H, t, J=3 Hz), 5.43 (1H, t, J=7 Hz), 7.29-7.48 (12H, m), 7.57-7.78 (8H, m)

1-5 (Step 1-5)

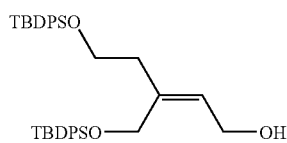

f

Pyridinium paratoluenesulfonate (90 mg, 0.36 mmol) was added to a solution (6 ml) of compound e (1.16 g, 1.67 mmol) in ethanol and the mixture was stirred at 60° C. for 3.5 hours. After the solution was cooled to room temperature, an aqueous saturated sodium bicarbonate solution was added thereto, followed by extraction with ethyl acetate. The organic layer was washed successively with water and a saturated aqueous NaCl solution and dried over anhydrous sodium sulfate. It was concentrated under reduced pressure and the crude product thus obtained was purified by column chromatography (silica gel, hexane-ethyl acetate 20:1) to obtain the compound f (825 mg, 81%) as a colorless oil.

Physicochemical Properties of Compound f
Molecular weight 608
FAB-MS (positive mode, matrix m-NBA) 631 (M+Na$^+$)
$^1$H-NMR (in deutero chloroform) chemical shift value δ: 1.01 (9H, s), 1.01 (9H, s), 1.23 (1H, t, J=6 Hz), 2.41 (2H, t, J=7 Hz), 3.75 (2H, t, J=7 Hz), 3.90 (2H, t, J=6 Hz), 4.14 (2H, s), 5.47 (1H, t, J=7 Hz), 7.29-7.47 (12H, m), 7.57-7.75 (8H, m)

1-6 (Step 1-6)

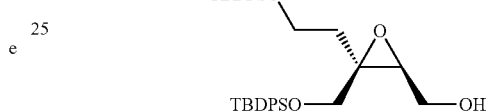

g

A round-bottom flask in which a rotor is placed was heated and dried under reduced pressure and then replaced with nitrogen and anhydrous dichloromethane (60 ml) was added thereinto, followed by cooling to −20° C. Titanium tetraisopropoxide (2.33 ml, 7.88 mmol) and diethyl L-(+)-tartrate (1.62 ml, 9.46 mmol) were successively added thereto and after stirring of the mixture for 15 minutes, a solution (30 ml) of compound f (4.80 g, 7.88 mmol) in dichloromethane was added thereto, followed by stirring of the mixture for 15 minutes. The mixture was cooled to −25° C. and tert-butyl hydroperoxide (5.25 ml, 15.8 mmol, 3N dichloromethane solution) was slowly added dropwise. After completion of the dropwise addition, the mixture was stirred at −20° C. for 2 hours and dimethyl sulfide (1.1 ml) was added thereto, followed by stirring of the mixture at the same temperature for additional one hour. After a 10% aqueous tartaric acid solution was added to the reaction solution and the mixture was stirred for 30 minutes, followed by stirring at room temperature for one hour. The organic layer was separated and an aqueous layer was extracted with a small amount of dichloromethane. The combined organic layer was dried over anhydrous sodium sulfate. The crude product obtained by concentration under reduced pressure was purified by column chromatography (silica gel, hexane-ethyl acetate 9:1) to obtain compound g (4.78 g, 97%) as a colorless oil. Asymmetric yield (>95% ee) was determined by NMR analysis of the corresponding MTPA ester.

Physicochemical Properties of Compound g
Molecular weight 624
FAB-MS (positive mode, matrix m-NBA) 647 (M+Na$^+$)
$^1$H-NMR (in deutero chloroform) chemical shift value δ: 1.02 (9H, s), 1.03 (9H, s), 1.72 (1H, t, J=6 Hz), 1.82 (1H, dt, J=14, 7 Hz), 2.23 (1H, dt, J=14, 6 Hz), 3.17 (1H, dd, J=6, 5 Hz), 3.55-3.79 (6H, m), 7.32-7.45 (12H, m), 7.60-7.65 (8H, m)

1-7 (Step 1-7)

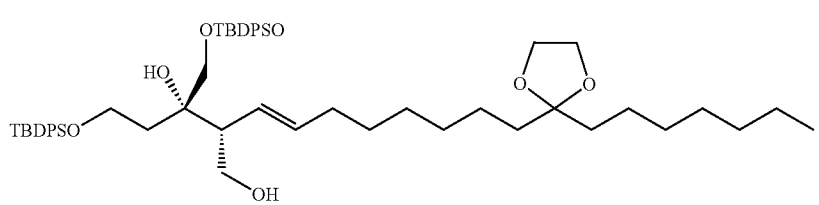

Under a nitrogen atmosphere, biscyclopentadienyl zirconium hydride chloride (10.11 g, 37.2 mmol) was added to a solution (100 ml) of compound α (10.45 g, 37.2 mmol) prepared in Step 2-3 of Preparation example 1 described later in anhydrous tetrahydrofuran at room temperature and the mixture was stirred for 30 minutes. The solution thus obtained was cooled to −78° C. and methyl magnesium chloride (24.7 ml, 74 mmol, 3N tetrahydrofuran solution) was added thereto, followed by stirring of the mixture for 5 minutes. Cuprous iodide (500 mg, 7.2 mmol) was added to this solution and the temperature of the mixture was gradually raised to −30° C. A solution (70 ml) of compound g (4.49 g) in anhydrous tetrahydrofuran was added thereto over 20 minutes and after completion of the dropwise addition, the mixture was stirred at −25° C. overnight. A saturated aqueous ammonium chloride solution was slowly added thereto to stop the reaction and the temperature of the mixture was gradually raised to room temperature. The mixture was stirred at room temperature for 10 hours and the precipitated white solid was removed by filtration by selite. The selite was washed well with ethyl acetate to separate the organic layer. The aqueous layer was extracted with a small amount of ethyl acetate and the combined organic layer was washed with a saturated aqueous ammonium chloride solution, followed by drying over anhydrous sodium sulfate. It was concentrated under reduced pressure and the crude product thus obtained was purified by column chromatography (silica gel, hexane-ethyl acetate 20:1-9:1) to obtain the compound h (5.96 g, 91%) as a pale yellow oil.

Physicochemical Properties of Compound h
Molecular weight 907
FAB-MS (negative mode, matrix m-NBA) 906 (M-H+)
$^1$H-NMR (in deutero chloroform) chemical shift value δ: 0.88 (3H, t, J=7 Hz), 0.99 (9H, s), 1.04(9H, s), 1.18-1.63 (22H, m), 1.78-2.01 (4H, m), 2.44-2.57 (1H, m), 3.00 (1H, t, J=6 Hz), 3.59-3.92 (10H, m), 4.28 (1H, s), 5.37-5.55 (2H, m), 7.29-7.65 (20H, m)

1-8 (Step 1-8)

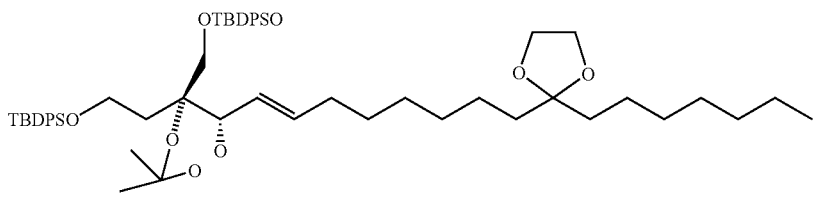

Compound h (5.30 g, 5.84 mmol) was dissolved in dichloromethane (200 ml) and 2,2-dimethoxypropane (150 ml) and pyridinium paratoluenesulfonate (15 mg, 0.058 mmol) were added thereto, followed by stirring of the mixture at room temperature overnight. A saturated sodium bicarbonate solution was added thereto to stop the reaction and the mixture was extracted twice with dichloromethane. It was dried over anhydrous sodium sulfate and concentrated under reduced pressure. The crude product thus obtained was purified by column chromatography (silica gel, hexane-ethyl acetate 20:1) to obtain the compound i (4.69 g, 86%) as a pale yellow oil.

Physicochemical Properties of Compound i
Molecular weight 947
FAB-MS (negative mode, matrix m-NBA) 946 (M-H$^+$)
$^1$H-NMR (in deutero chloroform) chemical shift value δ: 0.88 (3H, t, J=6 Hz), 1.02 (9H, s), 1.05(9H, s), 1.14-1.63 (28H, m), 1.78-2.16 (4H, m), 2.41-2.51 (1H, m), 3.47 (1H, d, J=10 Hz), 3.64-3.86 (6H, m), 3.92 (s, 4H), 5.36-5.42 (2H, m), 7.28-7.47 (12H, m), 7.61-7.69 (8H, m)

1-9 (Step 1-9)

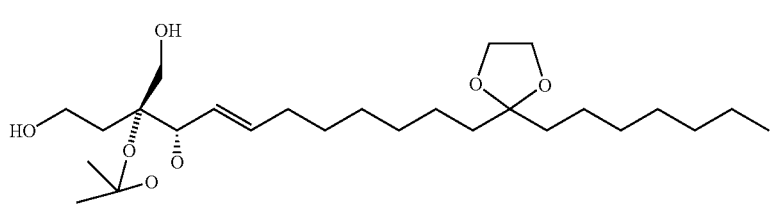

A solution (50 ml) of compound i (4.39 g, 4.64 mmol) in tetrahydrofuran was cooled to 0° C. and tetrabutylammonium fluoride (10.2 ml, 10.2 mmol, 1M tetrahydrofuran solution) and acetic acid (0.53 ml, 9.27 mmol) were added thereto. The temperature of the mixture was gradually raised to room temperature and the mixture was stirred for 2 days. A saturated aqueous ammonium chloride solution was added thereto and the mixture was extracted twice with dichloromethane. The combined organic layer was washed with an aqueous sodium bicarbonate solution and dried over anhydrous sodium sulfate. It was concentrated under reduced pressure and the crude product thus obtained was purified by column chromatography (silica gel, hexane:ethyl acetate 9:1-3:2) to obtain compound j (1.73 g, 81%) as a pale yellow oil.

Physicochemical Properties of Compound j

Molecular weight 470

FAB-MS (positive mode, matrix m-NBA) 493 (M+Na$^+$)

$^1$H-NMR (in deutero chloroform) chemical shift value δ: 0.88 (3H, t, J=6 Hz), 1.17-1.73 (26H, m), 1.91-2.16 (4H, m), 2.44 (1H, brs), 2.73 (1H, dt, J=6, 10 Hz), 2.95 (1H, brs), 3.48 (1H, d, J=11 Hz), 3.63-4.01 (m, 10H), 5.15 (1H, dd, J=15, 9 Hz), 5.55 (1H, dt, J=15, 7 Hz)

1-10 (Step 1-10)

tration. This procedure was carried out twice and the residue thus obtained was immediately used for the subsequent reaction.

The above crude dialdehyde was dissolved in 2-methyl-2-propanol (24 ml) and 2-methyl-2-butene (6 ml) and the mixture was cooled to approximately 5 to 7° C. An aqueous solution (7.45 ml) of sodium chlorite (745 mg, 8.24 mmol) and sodium dihydrogenphosphate (745 mg, 6.21 mmol) was slowly added dropwise to this solution. After 2 hours, the mixture was cooled to 0° C. and an aqueous sodium dihydrogenphosphate solution was added thereto to adjust the pH to approximately 5. The mixture was extracted with dichloromethane three times and after the combined organic layer was washed with an aqueous saturated NaCl solution, it was dried over anhydrous sodium sulfate. After filtration, a pale yellow oil obtained by concentration under reduced pressure was used for the subsequent reaction without further purification.

The crude dicarboxylic acid was dissolved in N,N-dimethylformamide di-tert-butylacetal (4.5 ml) and the mixture was stirred at 70° C. for one hour. The low boiling point compound was distilled off under reduced pressure. The residue was

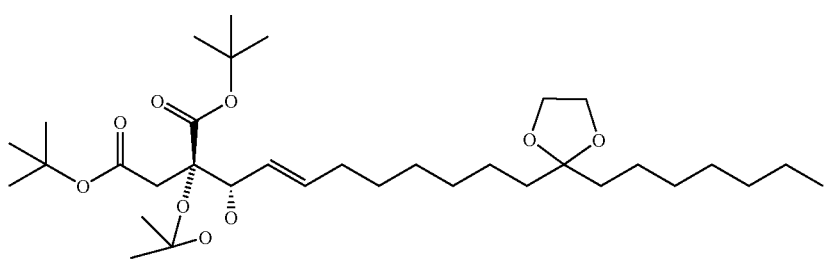

Under a nitrogen atmosphere, a solution (17 ml) of oxalyl chloride (0.575 ml, 6.6 mmol) in anhydrous dichloromethane was cooled to −78° C. and a solution (1 ml) of dimethyl sulfoxide (0.936 ml, 13.2 mmol) in dichloromethane was added dropwise thereto, followed by stirring of the mixture for 15 minutes. A solution (5 ml) of compound j (388 mg, 0.824 mmol) in dichloromethane was slowly added dropwise thereto. After the mixture was stirred at the same temperature for one hour, triethylamine (3 ml, 21.4 mmol) was added thereto, followed by stirring of the mixture for additional 30 minutes. The cooling bath was removed and a nitrogen stream was blown to the solution to remove the compound of low boiling point, followed by drying under reduced pressure. Diethyl ether (15 ml) was added to the residue and the insolubles were removed by filtration, followed by concenpurified by column chromatography (silica gel, hexane-ethyl acetate 20:1) to obtain compound k (340 mg, 60%) as a pale yellow oil.

Physicochemical Properties of Compound k

Molecular weight 610

FAB-MS (positive mode, matrix m-NBA) (M+H$^+$) 611, (M+Na$^+$) 633

$^1$H-NMR (in deutero chloroform) chemical shift value δ: 0.88 (3H, t, J=6 Hz), 1.18-1.64 (46H, m), 1.99 (2H, q, J=7 Hz), 2.69 (2H, ABq, J=15, 18 Hz), 2.93 (1H, q, J=7 Hz), 3.82-3.88 (2H, m), 3.92 (4H, s), 5.51-5.69 (2H, m)

1-11 (Step 1-11)

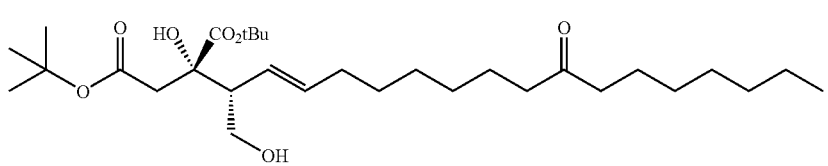

Compound k (340 mg, 0.556 mmol) was dissolved in tetrahydrofuran (1 ml) and 80% aqueous acetic acid solution (10 ml) was added thereto, followed by stirring of the mixture at room temperature for 3.5 hours. After the mixture was slowly added to a saturated sodium bicarbonate solution to neutralize acetic acid, the mixture was extracted twice with ethyl acetate. It was dried over anhydrous sodium sulfate, filtered and concentrated under reduced pressure to obtain compound l. (290 mg, 99%) as a pale yellow oil.

Physicochemical Properties of Compound 1
Molecular weight 526
FAB-MS (positive mode, matrix m-NBA) (M+H$^+$) 527, (M+Na$^+$) 549
$^1$H-NMR (in deutero chloroform) chemical shift value δ: 0.88 (3H, t, J=7 Hz), 1.18-1.68 (36H, m), 2.01 (2H, q, J=7 Hz), 2.25-2.41 (5H, m), 1.99 (1H, d, J=7 Hz), 2.04 (1H, d, J=7 Hz), 3.62-3.82 (2H, m), 3.99 (1H, s), 5.42 (1H, dd, J=9, 15 Hz), 5.58 (1H, dt, J=16, 6 Hz)

1-12 (Step 1-12)

low color of the reaction solution disappeared and a dark green precipitate appeared, and then the reaction was stopped. A saturated aqueous NaCl solution (20 ml) was added thereto and the mixture was extracted twice with dichloromethane. The combined organic layer was dried over anhydrous sodium sulfate. It was concentrated under reduced pressure and the residue was purified by silica gel column chromatography (dichloromethane-methanol 50:1-20:1) to obtain compound m (198 mg, 89%) as a pale yellow oil.

Physicochemical Properties of Compound m
Molecular weight 541
ESI (LC/MS positive mode) (M+H$^+$) 542

$^1$H-NMR (in deutero chloroform) chemical shift value δ: 0.88 (3H, t, J=6 Hz), 1.16-1.67 (36H, m), 1.99 (2H, q, J=6 Hz), 2.35 (4H, t, J=8 Hz), 2.70 (1H, d, J=16 Hz), 2.90 (1H, d, J=16 Hz), 3.28 (1H, d, J=9 Hz), 5.52 (1H, dd, J=9, 15 Hz), 5.68 (1H, dt, J=15, 5 Hz)

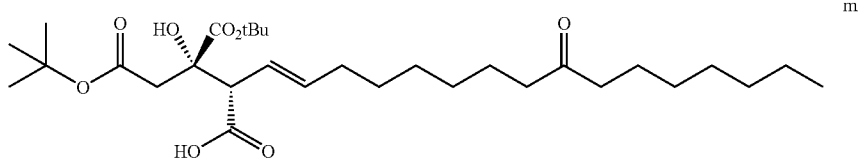

Acetone (45 ml) was cooled to 0° C. and Jones reagent (0.48 ml, 0.9 mmol, 1.89N) was added thereto. A solution (3 ml) of compound 1 (216 mg, 0.41 mmol) in acetone was slowly added dropwise to this mixture. After the mixture was stirred at the same temperature for one hour, an aqueous sodium hydrogensulfite solution was added thereto until yel- 1-13 (Step 1-13)

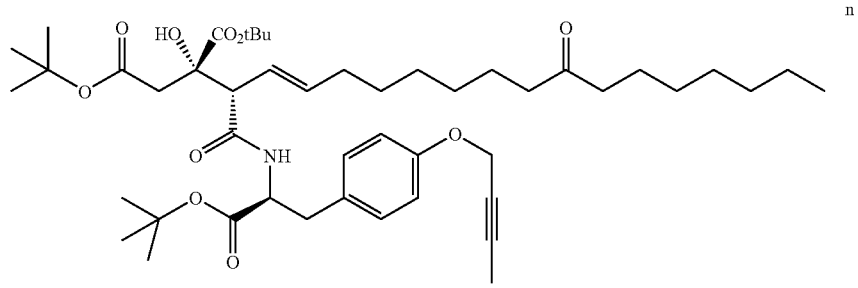

A solution (1 ml) of compound m (6.4 mg, 0.012 mmol) and (S)-4-(2-butynyloxy)phenylalanine t-butyl ester hydrochloride (4.6 mg, 0.014 mmol) in N,N-dimethylformamide was cooled to −10° C. and N,N-diisopropylethylamine (0.005 ml, 0.026 mmol) and O-(7-azabenzotriazol-1-yl)-N,N,N',N'-tetramethyluronium hexafluorophosphate (7.0 mg, 0.017 mmol) were successively added thereto. The temperature of the mixture was slowly raised to room temperature and the mixture was stirred overnight. An aqueous ammonium chloride solution was added thereto to stop the reaction and the mixture was extracted with ethyl acetate. After the organic layer was washed successively with water twice and a saturated aqueous NaCl solution, it was dried over anhydrous sodium sulfate. After filtration and concentration under reduced pressure, the residue was purified by silica gel thin layer chromatography (hexane-ethyl acetate 7:3) to obtain compound n (8.4 mg, 88%) as a colorless solid.

Physicochemical Properties of Compound n

ESI (LC/MS positive mode) 834 (M+Na$^+$)

$^1$H-NMR (in deutero chloroform) chemical shift value δ: 0.86 (3H, t, J=6 Hz), 1.12-1.68 (45H, m), 1.85 (3H, t, J=1.9 Hz), 1.90-2.03 (2H, m), 2.29-2.43 (4H, m), 2.59 (1H, d, J=16.5 Hz), 2.76 (1H, d, J=16.5 Hz), 2.97-3.14 (3H, m), 4.22 (1H, s), 4.57-4.74 (3H, m), 5.46 (1H, dd, J=9.2, 15.2 Hz), 5.64 (1H, dt, J=6.6, 15.2 Hz), 6.86 (2H, d, J=8.6 Hz), 7.01 (1H, d, J=7.9 Hz), 7.13 (2H, d, J=8.6 Hz)

1-14 (Step 1-14)

21

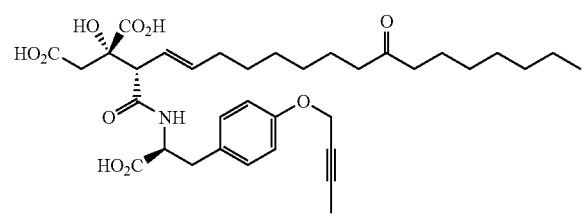

A solution (3 ml) of compound n (8.4 mg) in dichloromethane was cooled to 0° C. and anisole (0.01 ml) and trifluoroacetic acid (1 ml) were successively added thereto. The temperature of the mixture was slowly raised to room temperature and the mixture was stirred overnight. After the reaction solution was concentrated under reduced pressure, it was azeotropic treatment with benzene twice. The residue was purified by Megabond Elute Diol (500 mg, Varian) (dichloromethane-methanol=20:1) to obtain compound 21 (5.3 mg, 80%) as a colorless solid.

Physicochemical Properties of Compound 21

Molecular weight 643

ESI (LC/MS positive mode) 644 (M+H$^+$)

$^1$H-NMR (in methanol d-4) chemical shift value δ: 0.90 (3H, t, J=7 Hz), 1.19-1.38 (14H, m), 1.42-1.60 (4H, m), 1.82 (3H, t, J=2 Hz), 1.89-2.02 (2H, m), 2.44 (4H, t, J=7 Hz), 2.58 (1H, d, J=16 Hz), 2.78-2.98 (2H, m), 3.09-3.23 (2H, m), 4.53-4.67 (3H, m), 5.39-5.61 (2H, m), 6.83 (2H, d, J=9 Hz), 7.13 (2H, d, J=9 Hz)

Preparation Example 1

A synthesis method of compound a used in step 1-7 of Example 14 is explained in Preparation example 1.

Step 2-1

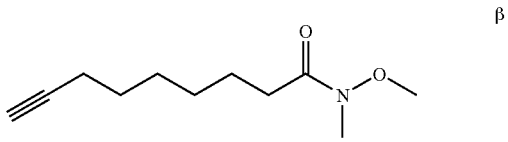

β

8-Nonynoic acid (50 g, 0.32 mol) was added dropwise to a solution (500 ml) of N,O-dimethylhydroxylamine hydrochloride (63.3 g, 0.65 mol), water-soluble carbodiimide hydrochloride (WSC.HCl) (124 g, 0.65 mol), 1-hydroxybenzotriazole (HOBt) (99.3 g, 0.65 mol) and N,N-diisopropylethylamine (DIPEA) (220 ml, 1.3 mol) in dichloromethane at 0° C. and the mixture was stirred at room temperature for 15 hours. The reaction solution was washed with a saturated aqueous ammonium chloride solution (400 ml), a saturated aqueous sodium hydrogencarbonate solution (400 ml) and a saturated aqueous NaCl solution (300 ml) After the organic layer was dehydrated and dried over anhydrous sodium sulfate, the solvent was distilled off under reduced pressure. The residue thus obtained was purified by column chromatography (Wako gel C-300, 500 g, Wako Purechemical) to obtain compound β (60 g, 94%) as a colorless oil from the hexane/ethyl acetate (20:1) eluting portion.

Physicochemical Properties of Compound β

Molecular weight 197

ESI (LC/MS positive mode) 198 (M+H$^+$)

$^1$H-NMR (in deutero chloroform) chemcial shift value δ: 1.30-1.70 (8H, m), 1.94 (1H, t, J=2.5 Hz), 2.19 (2H, dt, J=2.5, 7 Hz), 2.42 (2H, t, J=7.5 Hz), 3.18 (3H, s), 3.68 (3H, s)

21

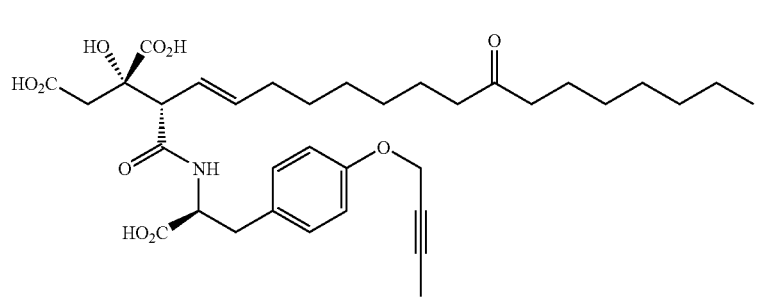

Step 2-2

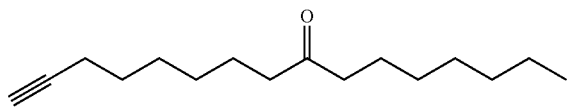

γ

1M Solution (100 mL, 0.1 mol) of n-heptyl magnesium bromide in diethyl ether was added dropwise to a solution (100 ml) of compound β as above (7 g, 0.035 mol) in tetrahydrofuran at −10° C. and the mixture was stirred at the same temperature for 2 hours and 30 minutes. A saturated aqueous ammonium chloride solution (30 ml) was added to the reaction solution and water (100 ml) was further added thereto, followed by stirring of the mixture at room temperature for 10 minutes. The mixture was diluted with water (300 ml) and extracted twice with ethyl acetate (400 ml). The organic layer was combined and washed with a saturated aqueous NaCl solution (30 ml). It was dehydrated and dried over anhydrous sodium sulfate and the solvent was distilled off under reduced pressure. The residue was purified by column chromatography (Wako gel C-300, 250 g, Wako Purechemical) to obtain compound γ (7.8 g, 93%) as a colorless oil from the hexane/ethyl acetate (100:1) eluting portion.

Physicochemical Properties of Compound γ
Molecular weight 236
EI-MS 236 (M+)
$^1$H-NMR (in deutero chloroform) chemcial shift value δ: 0.88 (3H, t, J=6.5 Hz), 1.23-1.63 (18H, m), 1.94 (1H, dt, J=0.5, 2.5 Hz), 2.18 (2H, dt, J=2.5, 7 Hz), 2.36-2.42 (4H, m)

Step 2-3

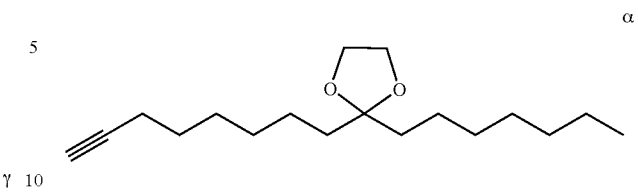

α

The above compound γ (7.8 g, 0.033 mol), ethylene glycol (18 mL, 0.33 mol) and toluenesulfonic acid monohydrate (125 mg, 0.66 mmol) were added to benzene (150 ml) and a reflux cooling tube mounted with Dien-Staak water separator was installed, followed by refluxing under heating for 20 hours. After allowed to stand for cooling, the reaction solution was washed with a saturated aqueous sodium hydrogencarbonate solution (30 ml), water (50 ml) and then a saturated aqueous NaCl solution (50 ml). The organic layer was dehydrated and dried over anhydrous sodium sulfate and the solvent was distilled off under reduced pressure. The residue thus obtained was purified by Megabond Elute Silica Gel (10 g, Varian) to obtain compound α (8.9 g, 97%) as a colorless oil from the hexane/ethyl acetate (20:1) eluting portion.

Physicochemical Properties of Compound a
Molecular weight 280
EI-MS 280 (M$^+$)
$^1$H-NMR (in deutero chloroform) chemical shift value δ: 0.88 (3H, t, J=6.5 Hz), 1.23-1.63 (22H, m), 1.93 (1H, t, J=2.5 Hz), 2.18 (2H, dt, J=2.5, 7 Hz), 3.92 (4H, s)

The compounds of the following Examples 15 to 19 were synthesized in the same manner as those described in Example 14.

Example 15

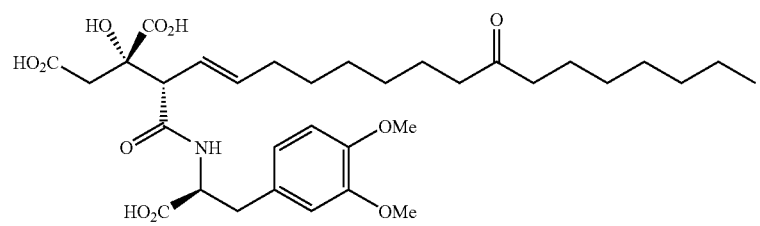

22

Physicochemical Properties of Compound 22

Molecular weight 635

ESI (LC/MS positive mode) 636 (M+H$^+$)

$^1$H-NMR (in methanol d-4) chemical shift value δ: 0.89 (3H, t, J=7.0 Hz), 1.17-1.36 (14H, m), 1.45-1.60 (4H, m), 1.90-2.02 (2H, m), 2.41-2.45 (4H, m), 2.53 (1H, d, J=16.0 Hz), 2.87 (1H, d, J=16.0 Hz), 2.92 (1H, dd, J=8.8, 14.0 Hz), 3.16-3.20 (2H, m), 3.78 (3H, s), 3.80 (3H, s), 4.67 (1H, dd, J=4.8, 9.2 Hz), 5.47-5.58 (2H, m), 6.75 (1H, m), 6.82-6.84 (2H, m)

Example 16

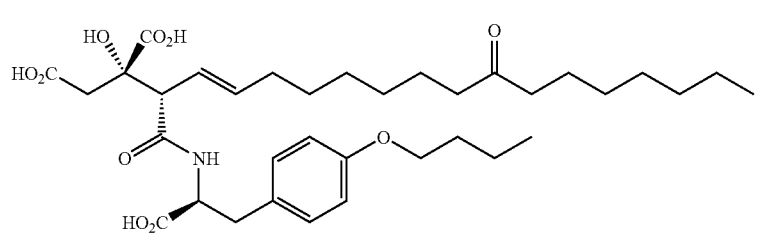

23

Physicochemical Properties of Compound 23
Molecular weight 647
ESI (LC/MS positive mode) 648 (M+H$^+$)
$^1$H-NMR (in methanol d-4) chemical shift value δ: 0.80 (3H, t, J=7 Hz), 0.98 (3H, t, J=7 Hz), 1.19-1.62 (20H, m), 1.91-2.03 (2H, m), 2.38-2.46 (4H, m), 2.57 (1H, d, J=8 Hz), 2.84-2.96 (2H, m), 3.11-3.23 (2H, m), 3.92 (2H, t, J=7 Hz), 4.63 (1H, dd, J=9, 5 Hz), 5.42-5.61 (2H, m), 6.80 (2H, d, J=9 Hz), 7.11 (2H, d, J=9 Hz)

Example 17

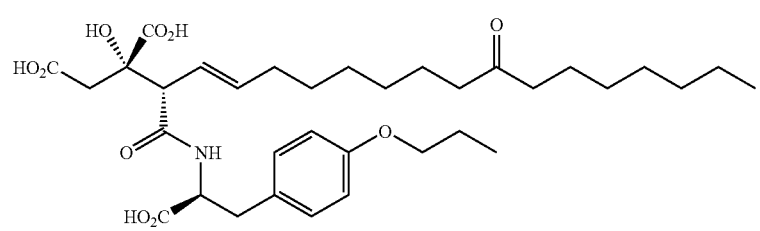

24

Physicochemical Properties of Compound 24
Molecular weight 633
ESI (LC/MS positive mode) 634 (M+H$^+$)
$^1$H-NMR (in methanol d-4) chemical shift value δ: 0.90 (3H, t, J=7 Hz), 1.03 (3H, t, J=7 Hz), 1.17-1.40 (14H, m), 1.43-1.60 (4H, m), 1.77 (2H, q, J=7 Hz), 1.91-2.01 (2H, m), 2.39-2.49 (4H, m), 2.56 (1H, d, J=17 Hz), 2.80-2.97 (2H, m), 3.10-3.20 (2H, m), 3.88 (2H, t, J=7 Hz), 4.64 (1H, dd, J=9, 5 Hz), 5.42-5.61 (2H, m), 6.80 (2H, d, J=9 Hz), 7.12 (2H, d, J=9 Hz)

Example 18

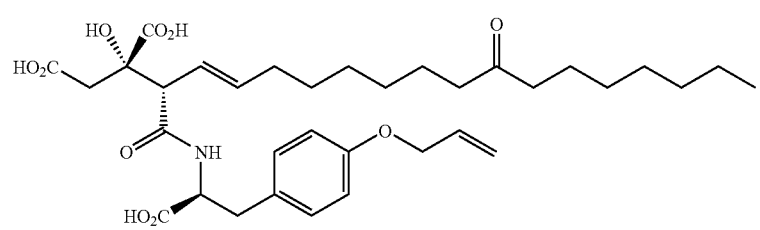

25

Physicochemical Properties of Compound 25
Molecular weight 631
ESI (LC/MS positive mode) 632 (M+H$^+$)
$^1$H-NMR (in methanol d-4) chemical shift value δ: 0.89 (3H, t, J=7 Hz), 1.14-1.38 (14H, m), 1.42-1.58 (4H, m), 1.89-2.01 (2H, m), 2.37-2.46 (4H, m), 2.57 (1H, d, J=16 Hz), 2.82-2.96 (2H, m), 3.11-3.22 (2H, m), 4.45-4.52 (2H, m), 4.63 (1H, dd, J=9, 4 Hz), 5.22 (1H, dd, J=10, 1 Hz), 5.37 (1H, dd, J=17, 1 Hz), 5.45-5.59 (2H, m), 5.97-6.10 (1H, m), 6.82 (2H, d, J=9 Hz), 7.14 (2H, d, J=9 Hz)

Example 19

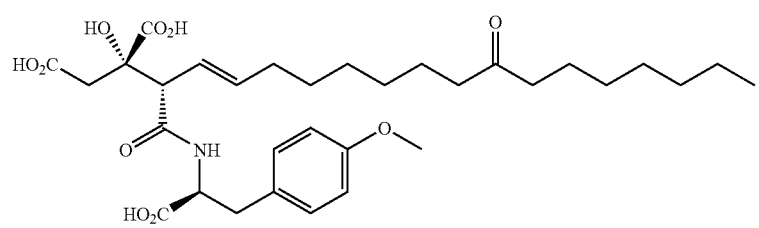

26

Physicochemical Properties of Compound 26
Molecular weight 605
ESI (LC/MS positive mode) 606 (M+H$^+$)
$^1$H-NMR (in methanol d-4) chemical shift value δ: 0.90 (3H, t, J=7 Hz), 1.18-1.40 (14H, m), 1.42-1.58 (4H, m), 1.91-2.01 (2H, m), 2.38-2.47 (4H, m), 2.53 (1H, d, J=15 Hz), 2.80-2.97 (2H, m), 3.11-3.21 (2H, m), 3.75 (3H, s), 4.64 (1H, dd, J=9, 5 Hz), 5.44-5.62 (2H, m), 6.81 (2H, d, J=9 Hz), 7.13 (2H, d, J=9 Hz)

Replicon Assay

A construct was prepared in which luciferase gene derived from firefly was inserted as a reporter gene in HCV-RNA to assay the number of copies of HCV-RNA. The luciferase gene was inserted in a form that fuses with the neomycin resistance gene directly below IRES (Internal Ribosome Entry Site) of HCV gene in accordance with the method of Krieger, et al. (J. Virol. 75: 4614). After synthesizing the RNA in vitro, it was introduced into Huh7 cells by electroporation followed by isolation as G418 resistant clone.

Firefly luciferase HCV replicon cells (3-1) were suspended in Dulbecco's MEM (Gibco Cat. No. 10569-010) containing 5% fetal calf serum (Hyclone Cat. No. SH30071.03) and inoculated into a 96-well plate at 5000 cells/well followed by culturing overnight at 5% $CO_2$ and 37° C. After about 20 hours, 10 μl of a diluted compound was added to each well followed by additional culturing for 3 days. Two series of the assay plates were prepared, and assay was conducted using white plates for one series while using clear plates for the other series. Following completion of culturing, the white plates were used with the Steady-Glo Luciferase Assay System (Promega Cat. No. E2520). More specifically, 100 μl of reagent was placed in each well and after mixing 3 to 4 times with a pipette and allowing to stand for 5 minutes, luminescence was measured with the 1450 MicroBeta TRILUX (WALLAC). The value in the absence of cell addition was used to indicate the background value, and that value was subtracted from all values to calculate the $IC_{50}$ value (concentration resulting in 50% inhibition) of the drug based on 0% inhibition for the value obtained in the absence of drug addition.

Cytotoxicity Test

The Cell Counting Kit-8 (Dojindo Cat. No. CK04) was used for measurement of cytotoxicity. More specifically, 10 μl of the Cell Counting Kit-8 was added to the clear plates followed by incubating at 37° C. for 30 to 60 minutes. Absorbance at a wavelength of 450 nm and control wavelength of 630 nm was measured with a 96-well plate reader. The value obtained in the absence of cell addition was used as a background value, and that value was subtracted from all values to calculate the $CC_{50}$ value (concentration resulting in 50% cell inhibition) of the drug based on 0% inhibition for the value obtained in the absence of drug addition.

| Compound No. | Replicon IC50 [μM] | Cytotoxicity CC50 [μM] |
|---|---|---|
| 1 | 0.002 | >5 |
| 2 | 0.128 | >1 |
| 3 | 0.076 | >1 |
| 4 | 0.103 | >1 |
| 5 | 0.082 | >1 |
| 6 | 0.007 | >1 |
| 7 | 0.002 | >5 |
| 8 | 0.005 | >5 |
| 9 | 0.020 | >5 |
| 10 | 0.245 | >50 |
| 11 | 0.262 | >5 |
| 12 | 0.072 | >5 |
| 13 | 0.1 | >50 |
| 14 | 0.020 | 22 |
| 15 | 0.020 | >50 |
| 21 | 0.001 | >5 |
| 22 | 0.017 | >1 |
| 23 | 0.001 | >1 |
| 24 | 0.002 | >1 |
| 25 | 0.001 | >1 |
| 26 | 0.003 | >1 |

INDUSTRIAL APPLICABILITY

The compounds of the present invention have extremely potent anti-HCV activity and HCV growth inhibitory effects, and since they also only demonstrate mild cytotoxicity in vivo, a pharmaceutical composition containing a compound of the present invention is extremely useful as an anti-HCV preventive/therapeutic agent.

The invention claimed is:

1. A compound represented by the following general formula (I):

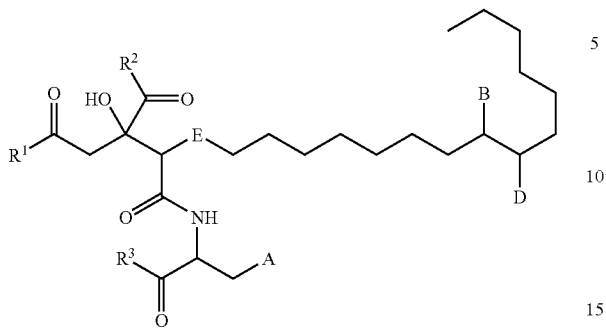

wherein

A represents a phenyl group substituted with —OX;

X represents a linear or branched alkynyl group having 2 to 8 carbon atoms;

B represents a hydrogen atom, a hydroxyl group, an oxo group, —N($R^4$)($R^5$), =N—OH, =N—$OR^6$ or a halogen atom;

$R^4$ and $R^5$ may be the same or different, and each represent a hydrogen atom, a linear or branched alkyl group having 1 to 6 carbon atoms, a linear or branched alkenyl group having 2 to 6 carbon atoms, or a linear or branched alkynyl group having 2 to 6 carbon atoms, or $R^4$ and $R^5$ together represent a 3 to 8 member ring;

$R^6$ represents a linear or branched alkyl group having 1 to 8 carbon atoms (which may be substituted with an amino group which may be mono- or di-substituted with a linear or branched alkyl group having 1 to 4 carbon atoms);

D represents a hydrogen atom or a hydroxyl group;

bond E represents a single bond or double bond;

$R^1$, $R^2$ and $R^3$ may be the same or different, and each represent a hydrogen atom, a hydroxyl group, an amino group (which may be mono- or di-substituted with a linear or branched alkyl group having 1 to 4 carbon atoms), —OZ, a linear or branched alkyl group having 1 to 4 carbon atoms, a linear or branched alkenyl group having 2 to 4 carbon atoms, or a linear or branched alkynyl group having 2 to 4 carbon atoms; and, Z represents a linear or branched alkyl group having 1 to 4 carbon atoms, a linear or branched alkenyl group having 2 to 4 carbon atoms, or a linear or branched alkynyl group having 2 to 4 carbon atoms, or a pharmaceutically acceptable salt thereof.

2. The compound of formula (I) according to claim 1 represented by the following general formula (I')

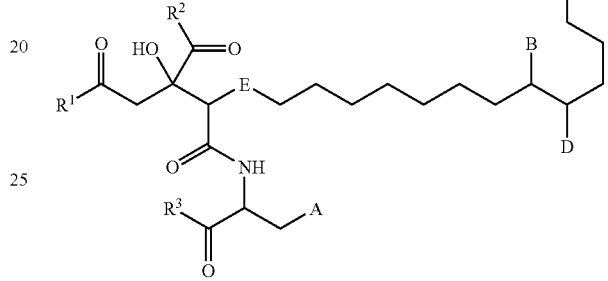

(wherein A, B, D, bond E, $R^1$, $R^2$ and $R^3$ are the same as described in claim 1), or a pharmaceutically acceptable salt thereof.

3. The compound of formula (I) according to claim 2 wherein B is an oxo group, or a pharmaceutically acceptable salt thereof.

4. The compound of formula (I) according to claim 3 wherein D is a hydrogen atom, and bond E is a double bond, or a pharmaceutically acceptable salt thereof.

5. The compound of formula (I) according to claim 4 wherein $R^1$, $R^2$ and $R^3$ are each a hydroxyl group, or a pharmaceutically acceptable salt thereof.

6. The compound of formula (I) according to claim 1 wherein X is a 2-butynyl group, or a pharmaceutically acceptable salt thereof.

7. A compound represented by the formula:
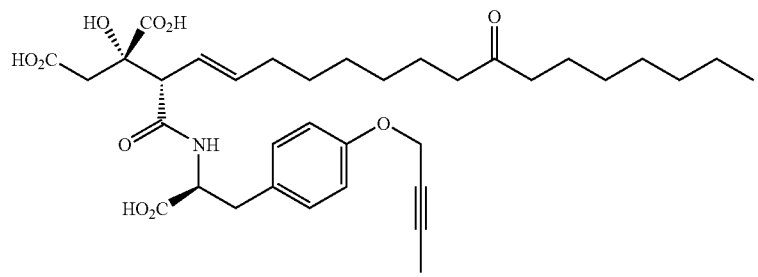
or a pharmaceutically acceptable salt thereof.
8. A pharmaceutical composition comprising a compound of formula (I) according to claim 1, or a pharmaceutically acceptable salt thereof.
* * * * *